US008554333B2

(12) United States Patent
Wu et al.

(10) Patent No.: US 8,554,333 B2
(45) Date of Patent: Oct. 8, 2013

(54) ADAPTABLE COMMUNICATION SENSITIVITY FOR AN IMPLANTABLE MEDICAL DEVICE

(75) Inventors: Yongjian Wu, Sunnyvale, CA (US);
Benjamin T. Persson, Sunnyvale, CA (US); Thanh Tieu, Milpitas, CA (US);
Dorin Panescu, San Jose, CA (US);
Devanshi Shah, Santa Clara, CA (US);
Lyle Frank Weaver, Woodside, CA (US)

(73) Assignee: Pacesetter, Inc., Sunnyvale, CA (US)

( * ) Notice: Subject to any disclaimer, the term of this patent is extended or adjusted under 35 U.S.C. 154(b) by 1221 days.

(21) Appl. No.: 12/179,336

(22) Filed: Jul. 24, 2008

(65) Prior Publication Data

US 2010/0023085 A1  Jan. 28, 2010

(51) Int. Cl.
*A61N 1/00* (2006.01)
*H04L 25/06* (2006.01)
*H04Q 5/22* (2006.01)
*G08B 1/08* (2006.01)

(52) U.S. Cl.
USPC ............. 607/60; 607/29; 607/30; 607/31; 607/32; 375/317; 340/10.33; 340/539.12

(58) Field of Classification Search
USPC ............ 607/60, 29–32; 340/10.33, 539.12; 375/317

See application file for complete search history.

(56) References Cited

U.S. PATENT DOCUMENTS

| 6,996,215 | B2 * | 2/2006 | MacConnell | 379/106.03 |
| 7,957,813 | B1 * | 6/2011 | Persson et al. | 607/60 |
| 2003/0097157 | A1 * | 5/2003 | Wohlgemuth et al. | 607/27 |
| 2004/0158299 | A1 * | 8/2004 | Patrias | 607/60 |
| 2007/0060053 | A1 * | 3/2007 | Haubrich et al. | 455/39 |
| 2007/0060978 | A1 * | 3/2007 | Haubrich et al. | 607/60 |
| 2007/0237212 | A1 * | 10/2007 | Kent et al. | 375/149 |

* cited by examiner

*Primary Examiner* — Niketa Patel
*Assistant Examiner* — William Levicky
(74) *Attorney, Agent, or Firm* — Steven M. Mitchell

(57) ABSTRACT

A wireless communication threshold for an implantable medical device is automatically adapted in an attempt to maintain optimum signal detection sensitivity. In some aspects, a threshold level may be adapted to account for current environmental conditions, implant conditions, device conditions, or other conditions that may affect the reception of wireless signals at the device. In some aspects, the determination of an optimum level for the threshold involves a tradeoff relating to effectively detecting target signals while avoiding detection of noise and/or interference. In some aspects, adaptation of a threshold may be based on maximum energy levels associated with one or more sets of RF energy sample data. In some aspects, adaptation of a threshold may be based on the number of false wakeups that occur during a period of time.

37 Claims, 10 Drawing Sheets

ADAPTABLE COMMUNICATION SENSITIVITY FOR AN IMPLANTABLE MEDICAL DEVICE

TECHNICAL FIELD

This application relates generally to implantable medical devices and, more specifically but not exclusively, to adapting a threshold that is used to determine whether an external device is transmitting to an implanted device.

BACKGROUND

Implantable medical devices may be employed in various applications. For example, an implantable cardiac device may perform one or more functions including sensing signals generated in a patient's heart, pacing the heart to maintain regular contractions, and providing defibrillation shocks to the heart. Similarly, an implantable stimulation device may be used to apply stimulation signals to a patients muscular tissue, neurological system, or some other area of the patient's body.

In practice, there may be a need to communicate with an implantable medical device after it has been implanted in a patient. For example, an external monitoring device located in a person's home, a doctor's office, a clinic, or some other suitable location may be used to retrieve information collected by and/or stored in the implanted medical device. In the case of an implanted cardiac device, such information may include sensed cardiac activity data that a treating physician may analyze to learn about the patient's health. Similarly, an external programming device located in any of the above locations may be used by a treating physician to change the operating parameters of the implanted medical device. Such parameters may include, for example, the timing or magnitude of stimulation pulses generated by the implanted medical device.

In a typical implementation, an implanted medical device utilizes radio frequency ("RF") telemetry to communicate with an external device. Consequently, the implanted medical device may include an RF transceiver that is adapted to transmit and receive RF signals. In such an implementation, however, it is generally desirable to leave the transceiver in a powered-off or low power state as much as possible since the transceiver may consume a relatively large amount of power. Here, it should be appreciated that the replacement of the battery in an implanted medical device involves a surgical procedure. Hence, long battery life is an important aspect of such a device.

Some types of implanted medical devices employ a wakeup scheme whereby an implanted device will periodically turn on its transceiver (e.g., its receiver) to determine whether an external device is attempting to establish a communication session. For example, whenever an external device wishes to establish communication with an implanted medical device, the external device may periodically transmit polling messages (e.g., connection requests) over one or more designated RF channels. Each of these polling messages may include information relating to establishing the communication such as, for example, an identifier that uniquely identifies the implanted medical device.

Every time the transceiver of the implanted medical device is turned on (e.g., at defined intervals), the transceiver may conduct an RF scan to determine whether the external device is transmitting polling messages. This may involve, for example, performing an ID scan that checks each RF channel for any messages that include an identifier associated with that particular implanted medical device. In the event such a message is detected, the implanted medical device transmits one or more signals (e.g., in accordance with a handshake protocol) to establish communication with the external device.

In practice, a transceiver of an implanted medical device may consume a relatively significant amount of power even when a conventional wakeup scheme is used. For example, it may be desirable for an implanted medical device to be able to respond to polling messages within a relatively short period of time, for example, so that a treating physician need not wait several minutes to establish communication with the implanted medical device. The implanted medical device may therefore perform its scans at relatively frequent intervals to achieve a quick response time. Such frequent scanning may, however, increase the amount of power consumed by the implanted medical device.

In some cases, a wakeup scheme may involve staged detection to reduce the amount of power consumed by the implanted medical device. For example, such a scheme may employ a simple detection stage that samples RF energy and a more robust scanning stage that analyzes any detected signals to determine whether these signals are from an external device that is attempting to establish communication with the implanted medical device. Here, the simple detection stage may repeatedly perform an energy "sniff" in the RF channel or channels of interest. By starting a detection search with this low-level and relatively coarse energy assessment stage, the implanted medical device may avoid using the relatively high power robust scanning stage during those times when the external device is not transmitting a signal which, in practice, is usually the case for most of the lifetime of the implanted medical device. Hence, additional power savings may be achieved with this type of wakeup scheme in comparison to a wakeup scheme that does not employ staged detection.

SUMMARY

A summary of several sample aspects of the disclosure and embodiments of an apparatus constructed or a method practiced according to the teaching herein follows. It should be appreciated that this summary is provided for the convenience of the reader and does not wholly define the breadth of the disclosure. For convenience, one or more aspects or embodiments of the disclosure may be referred to herein simply as "some aspects" or "some embodiments."

The disclosure relates in some aspects to adaptation of a wireless communication threshold for an implantable medical device. Such a threshold may be used, for example, to determine whether an external wireless device is attempting to establish communication with an implanted device. In some aspects, the implanted device may use the threshold to determine when to move from one communication mode to another communication mode. For example, during a low power energy sensing (e.g., sniffing) mode a receiver of the implanted device may be enabled intermittently. Any signal energy detected during the sniffing mode may be compared with the threshold to determine whether to transition to a more robust communication mode (e.g., which may be less power efficient). During the more robust mode, the receiver may be enabled for longer periods of time to receive more signal information and/or the received signals may be processed more extensively in an attempt to recover information conveyed by the signals.

In some aspects, the threshold may be adapted in an attempt to determine an optimum threshold level in view of current conditions at the implanted device. For example, the threshold level may be automatically adapted to account for current environmental conditions, implant conditions, device conditions, or other conditions that may affect reception of wireless signals at an implanted device.

In some aspects, the determination of an optimum value for the threshold involves a tradeoff relating to the detection sensitivity of the receiver. For example, the use of a higher sensitivity may enable more effective detection of a target signal from the external device. However, a high sensitivity also may result in detection of signals that are not desired (e.g., noise or interfering signals from some other device). The detection of these undesirable signals may, in turn, result in false wakeups where the implanted device unnecessarily transitions to the higher power mode to acquire and process signals that are not target signals. In view of the above, the adaptation process may be configured to set the threshold to a lower value when the implanted device is operating in a low noise environment and to a higher value when the device is operating in a noisier environment.

The disclosure relates in some aspects to adaptation of a threshold based on at least one maximum energy level derived from one or more sets of energy sample data (e.g., representative of intrinsic noise and/or environmental noise). For example, an implanted device may acquire a defined number of samples and select a threshold value based on a maximum energy level associated with the samples. In this way, the threshold may be set to a value that is slightly higher than a noise and/or interference floor associated with the sample data. In some aspects, the maximum energy level may be selected from a plurality of maximum values associated with different data sets. In some aspects, a data set may comprise histogram information. For example, the maximum energy level may be derived from a tail (e.g., a first tail) of a set of histogram data.

The disclosure relates in some aspects to adaptation of a threshold based on the number of false wakeups that occur during a period of time. For example, upon detection of a given number of false wakeups, an implanted device may increase a threshold, temporarily cease sniffing operations, disable wakeup detection, or perform some other suitable operation.

BRIEF DESCRIPTION OF THE DRAWINGS

These and other features, aspects, and advantages will be more fully understood when considered with respect to the following detailed description, the appended claims, and the accompanying drawings, wherein:

Figure 1:
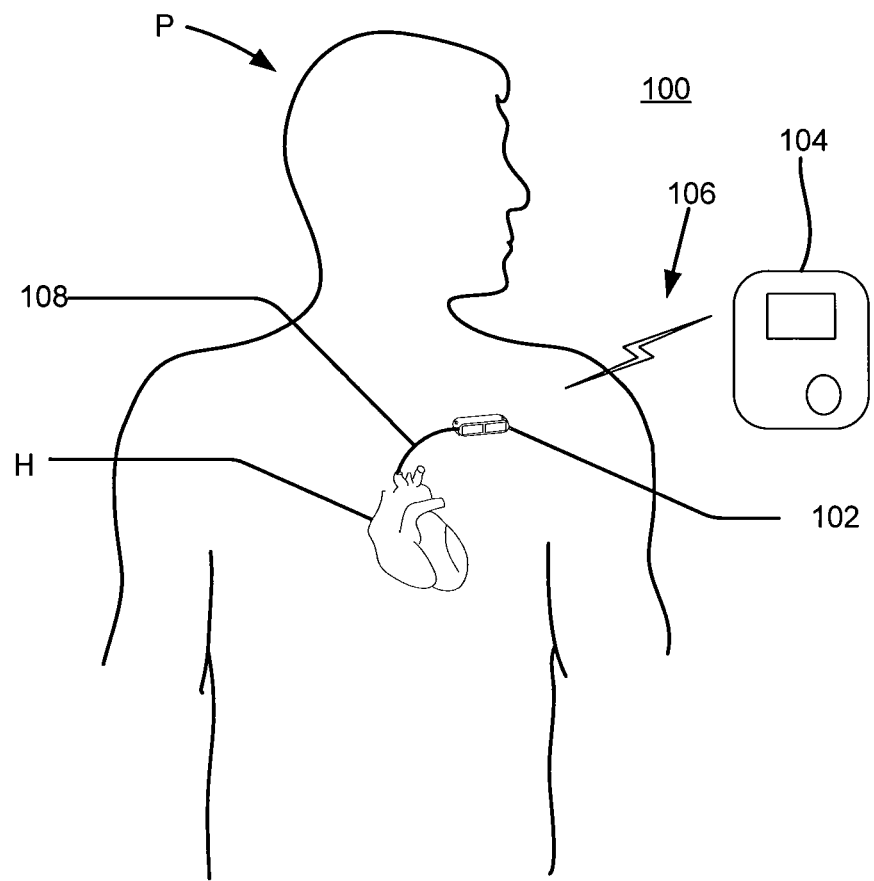
FIG. 1 is a simplified diagram of a communication system including an implantable medical device and an external device.

In accordance with common practice the various features illustrated in the drawings may not be drawn to scale. Accordingly, the dimensions of the various features may be arbitrarily expanded or reduced for clarity. In addition, some of the drawings may be simplified for clarity. Thus, the drawings may not depict all of the components of a given apparatus or method. Finally, like reference numerals may be used to denote like features throughout the specification and figures.

DETAILED DESCRIPTION

The description that follows sets forth one or more illustrative embodiments. It will be apparent that the teachings herein may be embodied in a wide variety of forms, some of which may appear to be quite different from those of the disclosed embodiments. Consequently, the specific structural and functional details disclosed herein are merely representative and do not limit the scope of the disclosure. For example, based on the teachings herein one skilled in the art should appreciate that the various structural and functional details disclosed herein may be incorporated in an embodiment independently of any other structural or functional details. Thus, an apparatus may be implemented or a method practiced using any number of the structural or functional details set forth in any disclosed embodiment(s). Also, an apparatus may be implemented or a method practiced using other structural or functional details in addition to or other than the structural or functional details set forth in any disclosed embodiment(s).

FIG. 1 illustrates a simplified diagram of a communication system 100 including an implantable medical device 102 that is implanted within a patient P and a device 104 that is located external to the patient P. The implanted device 102 and the external device 104 may communicate with one another via a wireless communication link 106 (as represented by the illustrated symbol).

In this example, the implanted device 102 is an implantable cardiac device including one or more leads 108 that are routed to the heart H of the patient P. For example, the implanted device 102 may be a pacemaker, an implantable cardioverter defibrillator, or some other similar device. It should be appreciated, however, that the implanted device 102 may take other forms. For example, in some embodiments the implanted device 102 may be a neuro-stimulation device or some other type of implantable device.

The external device 104 also may take various forms. For example, the external device 104 may be a base station, a programmer, a home safety monitor, a personal monitor, a follow-up monitor, a wearable monitor, or some other type of device that is configured to communicate with an implanted device.

In a typical embodiment, the communication link 106 is an RF link. In some embodiments the communication link 106 may operate within the medical implant communication service ("MICS") band. It should be appreciated, however, that the teachings herein may be employed in conjunction with other RF bands such as a band in the 2.45 GHz range or some other band. In other embodiments the communication link 106 may take other forms including, for example, an inductive telemetry link.

The communication link 106 may be used to transfer information between the devices 102 and 104 in conjunction with various applications such as surgical procedures, clinical visits, data acquisition, remote follow-up, remote home-monitoring, and portable or wearable patient monitoring/control systems. For example, when information needs to be transferred between the devices 102 and 104, the patient P moves into a position that is relatively close to the external device 104, or vice versa. As will be discussed in more detail below, the external device 104 may then be configured to transmit periodic signals to the implanted device 102 to initiate communication between the devices 102 and 104.

The implanted device 102 may employ a wakeup scheme to reduce power consumption associated with determining whether the external device 104 is attempting to establish communication with the implanted device 102. For example, a transceiver component (e.g., a receiver) of the implanted device 102 that is used for communicating with the external device 104 may normally be turned off or set to a low power mode in some other manner. This component may then be turned on from time to time to sense for signals from the external device 104. In some embodiments the wakeup scheme employs staged detection whereby the result of a low-level scan (e.g., an RF energy sniff) during a low power operational mode is used to determine whether to transition to another operational mode to conduct a high-level scan (e.g., a full scan of one or more communication channels).

The detection scheme may be adaptive whereby one or more parameters are adjusted to increase the likelihood of detection of a target signal from the external device 104 and to reduce any adverse consequences (e.g., increased power consumption) that result from detection of non-target signals. For example, a threshold used during the low-level scan may be adapted to reduce the number of false wakeups that occur at the implanted device 102.

In some aspects, a threshold may be defined by acquiring discrete samples of environmental and/or intrinsic noise (e.g., over a defined period of time), determining energy level values of those samples, taking a statistical measure of the energy sample values, and adding a defined increment to the statistical measure to provide a threshold value. In some aspects, the statistical measure may be based on a maximum sample value derived from the samples. In some aspects, the statistical measure may be based on zero value and non-zero value sample sequences (e.g., of a histogram) associated with the defined number of samples.

Figure 2:
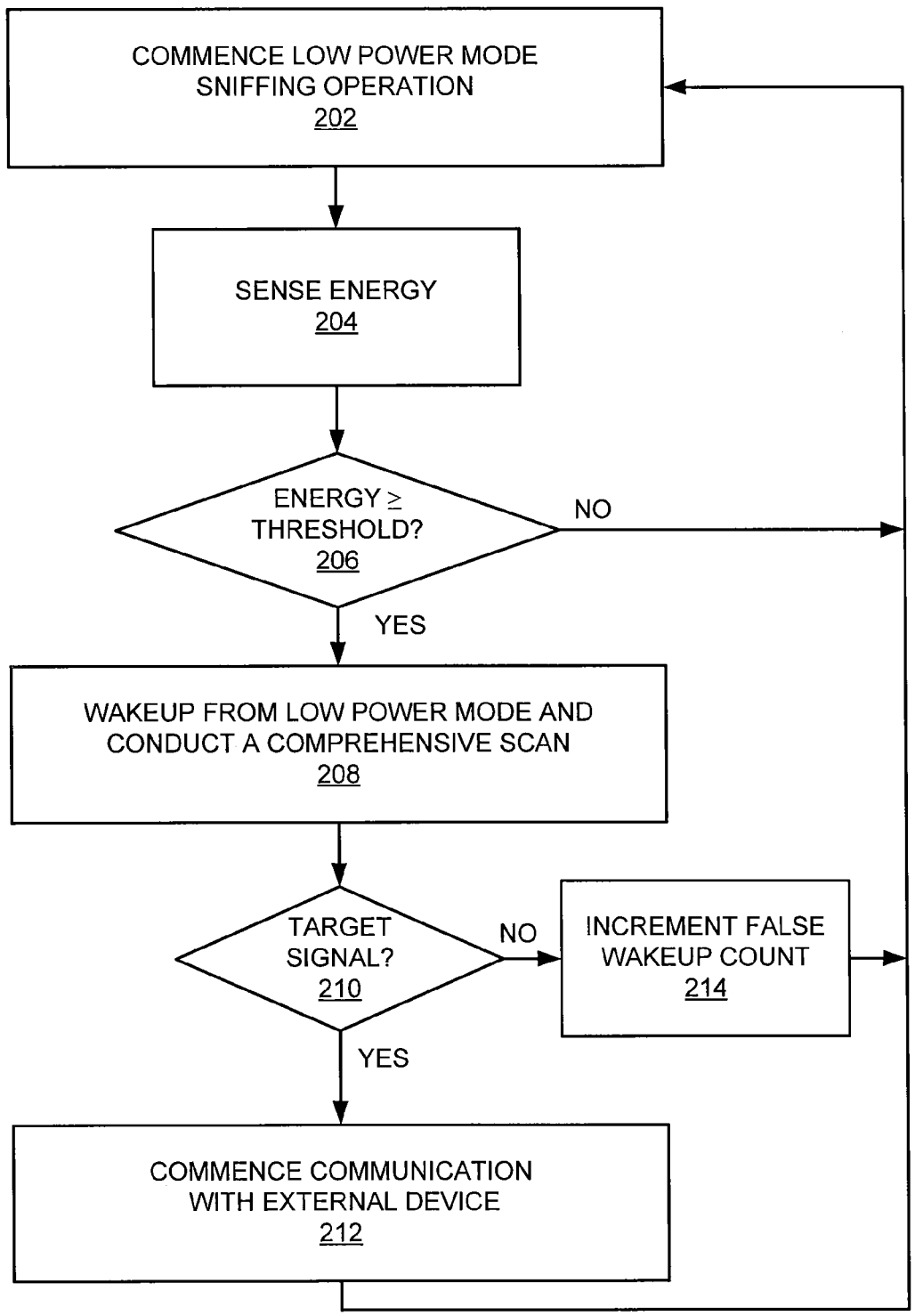
FIG. 2 is a flowchart of an embodiment of operations that may be performed to establish communication between an implantable medical device and an external device.
Figure 3:
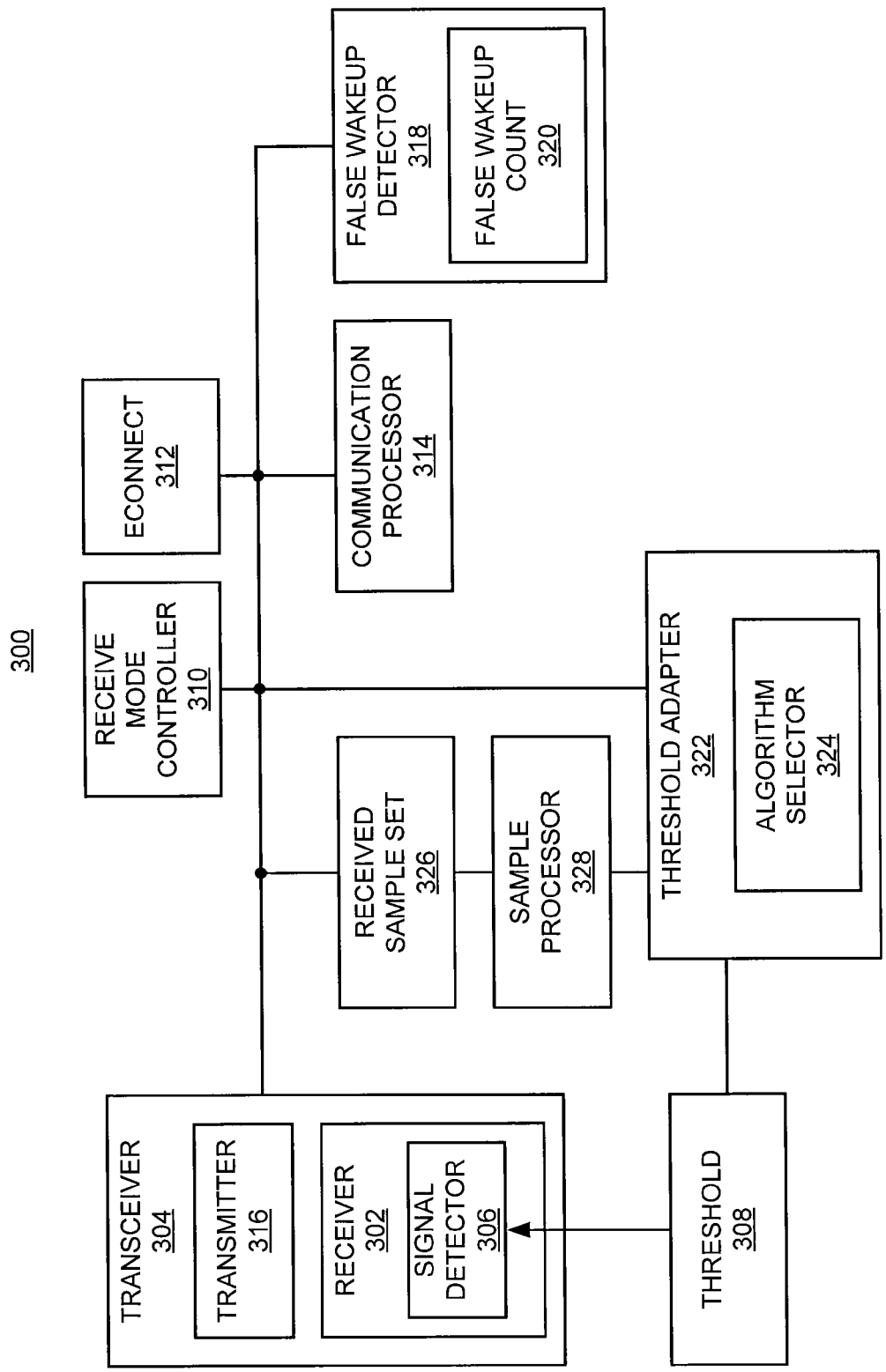
FIG. 3 is a simplified block diagram of an embodiment of communication-related components of an external device.
Figure 4:
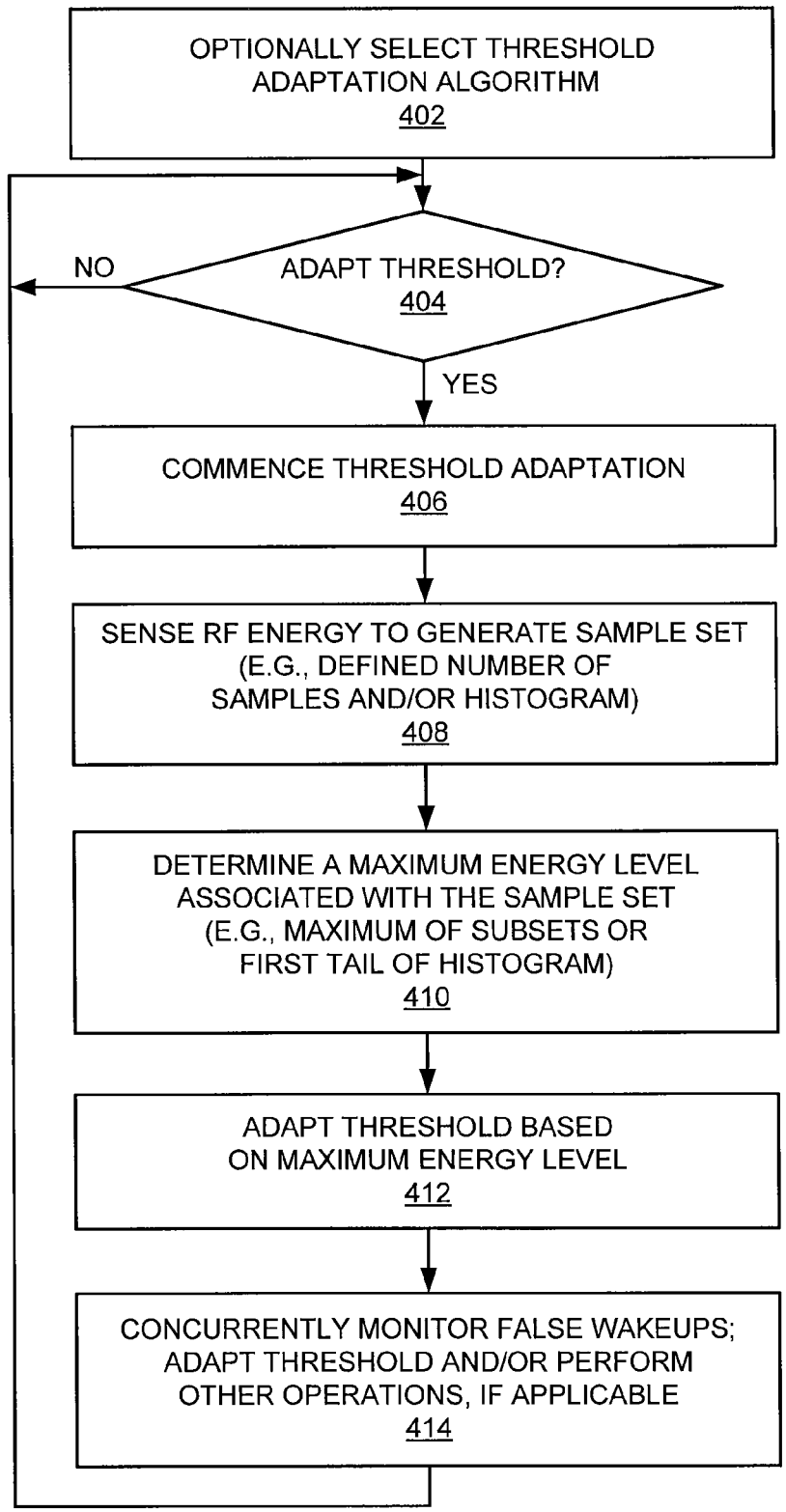
FIG. 4 is a flowchart of an embodiment of operations that may be performed to adapt a threshold.

These and other detection techniques will now be described in more detail in conjunction with FIGS. 2, 3, and 4. FIG. 2 illustrates several sample operations that may be performed by an implanted device to establish communication with an external device. FIG. 3 illustrates several sample components of an embodiment of a device 300 (e.g., communication components of the implanted device 102). FIG. 4 illustrates several sample operations that may be performed by an implanted device to adapt a threshold.

For convenience, the operations of FIG. 2 (or any other operations discussed or taught herein) may be described as being performed by specific components (e.g., components of the device 300). It should be appreciated, however, that these operations may be performed by other types of components and may be performed using a different number of components. It also should be appreciated that one or more of the operations described herein may not be employed in a given implementation.

Referring initially to FIG. 2, the implanted device 102 may wake up on a repeated basis to determine whether the external device 104 is transmitting signals in an attempt to establish a communication session. As represented by block 202, the implanted device 102 may thus commence a low power mode RF sniffing operation at designated times. Referring to the example of FIG. 3, a receiver component 302 in a transceiver 304 may be intermittently activated (e.g., powered on according to a defined scan interval) to scan for signals within a given RF frequency band.

In some embodiments, at a given point in time the devices 102 and 104 may communicate via any one of several channels that are defined for a given frequency band. In these cases, the devices 102 and 104 may elect to use a channel that provides the most effective communication medium (e.g., that has the least amount of interference) at a given point in time. In some embodiments the devices 102 and 104 may communicate via any of the channels defined for the MICS band. When the external device 104 initially attempts to establish a communication session with the implanted device 102, the external device 104 selects a particular channel on which to transmit its request messages. Consequently, during the low power sniff operation, the receiver 302 may be configured to scan each of the channels of the designated communication band (e.g., separately or in one or more groups) to determine whether the external device 104 is currently sending messages over any of the channels.

As represented by block 204, the receiver 302 thus attempts to detect signal energy within a certain frequency range for a defined period of time. The signal detection of block 204 may advantageously be a relatively low power operation. Here, rather than scanning for a long period of time in an attempt to acquire an entire message transmitted by the external device 104, the receiver 302 may sense for a short period of time (e.g., a few milliseconds) and utilize a low power signal detector 306 (e.g., an energy detector) to detect a signal. For example, the signal detector 306 may be configured to simply detect the magnitude of a signal, an energy level of a signal, or some other suitable attribute of a received signal. Hence, the operation of block 204 may involve partially "waking up" the device 300 since, for example, full operation of its communication components may not be needed at this point. In some embodiments such a low power, partially awakened mode may be invoked by enabling (e.g., powering on) only a portion of the communication components of the device 300 (e.g., component 302 or component 304). Also, the low power, partially awakened mode may be invoked by modulating the duration for which one or more communication components are enabled (e.g., powered on). For example, the partially awakened mode may involve repeatedly enabling, over the course of a scan interval, one or more communication components for a relatively short period of time. In this case, power savings may thus be achieved by not turning on the component or components for the entire interval.

As represented by block 206 of FIG. 2, the signal detector 306 may compare the detected signal, if any, with a threshold 308. For example, in some embodiments a received signal strength indication ("RSSI") associated with the detected signal may be compared with the threshold 308. Such a comparison may thus serve as a basis for determining whether to perform a more robust (e.g., comprehensive) scan.

In the event the designated signal property (e.g., RSSI) detected at block 204 is less than the threshold 308 at block 206, an assumption may be made that the external device 104 is not transmitting a target signal to the implanted device 102.

In this case, the operational flow may return to block 202 to wait for the next RF sniff interval (e.g., by operation of a receive mode controller 310).

In the event the signal property (e.g., RSSI) detected at block 204 equals or exceeds the threshold 308 at block 206, an assumption may be made that the signal is from the external device 104. Consequently, as represented by block 208 the device 300 (e.g., by operation of the receive mode controller 310) may wakeup from the low power mode to perform a more comprehensive scan on one or more designated channels for signals from the external device 104. In some embodiments, the channel or channels scanned at block 208 may be the same as those scanned at block 204. Here, the receiver 302 may be adapted to scan each channel for a sufficiently long period of time to acquire any messages transmitted by the device 104.

To accomplish such a comprehensive scan, the operation of block 208 may thus involve "waking-up" one or more additional components of the device 300. For example, the higher-power, fully awakened mode may be invoked by enabling (e.g., powering on) all or substantially all of the communication components of the device 300. In addition, in contrast with certain embodiments of the partially awakened mode, the fully awakened mode may involve continually enabling one or more communication components over the course of an entire scan interval. Thus, the comprehensive scan of block 208 may be longer in duration and/or may consume more power than the sensing operations of block 204.

As represented by block 210, the receiver 302 and/or a communication processor 314 may be adapted to analyze a received signal to determine whether it is a target signal from the external device 104. To this end, the receiver 302 may be configured to extract any messages that are encoded in the signals. The communication processor 314 may then determine whether the message includes an identifier that identifies the implanted device 102.

As discussed in more detail below, the receiver 302 also may maintain a record of the signal property (e.g., RSSI level) that resulted in detection of a target signal. In some aspects, this type of information may be used, for example, to set the level of the threshold 308. In the example of FIG. 3, this information is designated as econnect 312 (e.g., the energy associated with a successful connection).

As represented by block 212, in the event a message destined for the implanted device 102 is detected, the implanted device 102 may commence communication with the external device 104. For example, the communication processor 314 may proceed to establish a connection with the external device 104 by generating an appropriate response message and sending the message to the external device 104 via a transmitter 316.

As represented by block 214, in the event a target signal is not detected at block 210, a false wakeup condition may be indicated. For example, the presence of noise or in-band communication by other devices may result in a successful comparison at block 206 and, consequently, an unwanted transition to a high-level scan at block 208. As will be discussed in more detail below, the implanted device 102 may thus comprise a false wakeup detector 318 that maintains a false wakeup count 320. If the false wakeup detector 318 detects a given number of false wakeups (e.g., as defined by a false wakeup threshold) within a defined period of time, the threshold 308 may be adapted and/or some other course of action may be taken to reduce the number of occurrences of such unwanted high-level scans. For example, the threshold 308 may be adapted (e.g., increased) so that the receiver 302 is less sensitive to noise or other signals within the frequency band of interest. In some embodiments, the threshold 308 may not be adapted in the event the false wakeup is associated with a signal from a compatible external device (e.g., an external device made by the same manufacturer as the external device 104) since the detected energy level may correctly correspond to a target signal.

In some embodiments the false wakeup threshold may be adaptable. For example, the false wakeup threshold may be adapted based on current and/or past environmental conditions. In some implementations the false wakeup threshold is adapted based on the frequency of false wakeups. For example, if false wakeups have not been detected for a relatively long period of time (e.g., one week or one month), the false wakeup threshold may be increased.

In some embodiments, the false wakeup detector 318 may track the number of false wakeups that occur over a longer period of time and cease energy sniffing operations in the event this number exceeds a defined threshold value (e.g. 100 or 1000). For example, if this threshold value is exceeded during a defined period of time, the implanted device 102 may cease background sniffing operations and just rely on a scheduled wakeup scan (e.g., that occurs every two hours) to determine whether the external device 104 is attempting to establish communication. The scheduled wakeup scan is described in more detail below. The background sniffing operations may then be re-enabled, for example, by reprogramming the implanted device 102 (e.g. via telemetry), or when a scheduled wakeup occurs. In some aspects the threshold value may be programmable. For example, in some implementations the threshold value may be adjusted by a defined amount depending on a current operating condition (e.g., the rate that false wakeups are occurring) or some other factor. In some implementations the threshold value may be set to or adjusted up to a maximum value.

After the false wakeup-invoked operations are performed, the operational flow may return to block 202 to wait for the next RF sniff interval (e.g., by operation of the receive mode controller 310).

As mentioned above, in some aspects the threshold used for the signal detection operation may be adaptable. For example, due to one more factors such as RF interference (e.g., the background radio noise level) in the current environment, intrinsic noise of the implanted device 102, and implant site characteristics. As an example of the latter factor, the electrical characteristics of the tissue at the implant site or the electrical interface of the tissue and one or more conductive surfaces of the implanted device may affect the reception of signals at the implanted device. Thus, different thresholds may be defined for devices implanted in different patients, even under the same environmental conditions and given identical device characteristics. Similarly, even for a single device implanted in a given patient, one threshold value may be specified immediately after implant and a different threshold specified at some later point in time. As a result of the above factors, it is desirable to automatically adapt the threshold 308 (e.g., a sniff energy threshold) to limit the number of false wakeups while maintaining good sensitivity to target signals from the external device 104.

FIG. 4 illustrates several sample operations that may be performed to adapt a threshold. Again, for illustration purposes, the operations of FIG. 4 may be described in the context of the system 300 of FIG. 3 which includes a threshold adapter 322.

In some embodiments the implanted device 102 may support multiple threshold adaptation algorithms. Accordingly, as represented by block 402 of FIG. 4, a particular algorithm may be selected for the threshold adaptation operations. For example, in some embodiments the algorithm may be selected by a treating physician during implant, during a clinical follow-up, or at some other time. As discussed below, the implanted device 102 may include functionality that enables the implanted device 100 to be programmed (e.g., to use the selected algorithm).

A particular algorithm may be selected based on various factors. For example, certain algorithms may result in the implanted device 102 having higher detection sensitivity than other algorithms. Hence, a decision may be made to use a given algorithm if it is determined that the implanted device 102 may operate in a particular environment (e.g., a low noise environment) the majority of the time. Several examples of threshold adaptation algorithms are described below in conjunction with FIGS. 5-9.

In some embodiments the implanted device 102 may automatically select the algorithm. For example, the implanted device 102 may include an algorithm selector 324 that is configured to select the algorithm based on the characteristics of the current environment (e.g., current RF noise levels), prior detection performance (e.g., the number of false wakeups or missed target signals), power consumption considerations, or some other suitable operating characteristic. To this end, the implanted device 102 may include appropriate functionality to identify one or more of the above operating characteristics.

As represented by block 404 of FIG. 4, at some point in time the threshold adapter 322 may elect to adapt the threshold 308. As will be discussed in more detail in conjunction with FIGS. 5-9, in some aspects the threshold 308 may be adapted on a repeated (e.g., periodic) basis. In addition, in some cases the threshold 308 may be adapted if a defined number of false wakeups occur within a defined period of time.

In the event threshold adaptation is commenced at block 406, the receiver 302 may be configured to sense signals (e.g., sniff energy in one or more RF channels) to generate one or more sets of energy samples 326 (block 408). As will be discussed in more detail below, each sample set 326 may comprise a defined number of samples. In addition, in some implementations a sample set 326 may comprise a histogram. In some aspects, the operation of block 408 may comprise a background operation that is invoked at defined intervals (e.g., a sniff comprising 8 samples is acquired every 30 seconds).

As represented by block 410, a sample processor 328 may process the sample set(s) 326 to determine a maximum energy level associated with the sample set(s) 326. For example, as described below in conjunction with FIGS. 5-7, in some embodiments the sample processor 328 may determine a maximum energy level by identifying a maximum value from one or more sample sets 326. As described below in conjunction with FIGS. 8 and 9, in some embodiments the sample processor 328 may determine a maximum energy level by identifying a tail (e.g., the first tail) of a histogram.

As represented by block 412, the threshold adapter 322 may define (e.g., update) the threshold 308 based on the sample set(s) 326. For example, the threshold adapter 322 may set the threshold 308 to the maximum energy level from block 410 plus a suitable safety margin.

As represented by block 414, the false wakeup detector 318 may concurrently monitor for false wakeups (e.g., as described herein). In the event too many false wakeups are detected, threshold adapter 322 may further adapt the threshold 308. In addition, as will be described below, the implanted device 102 may perform other operations as a result of the detection of too many false wakeups.

Figure 5:
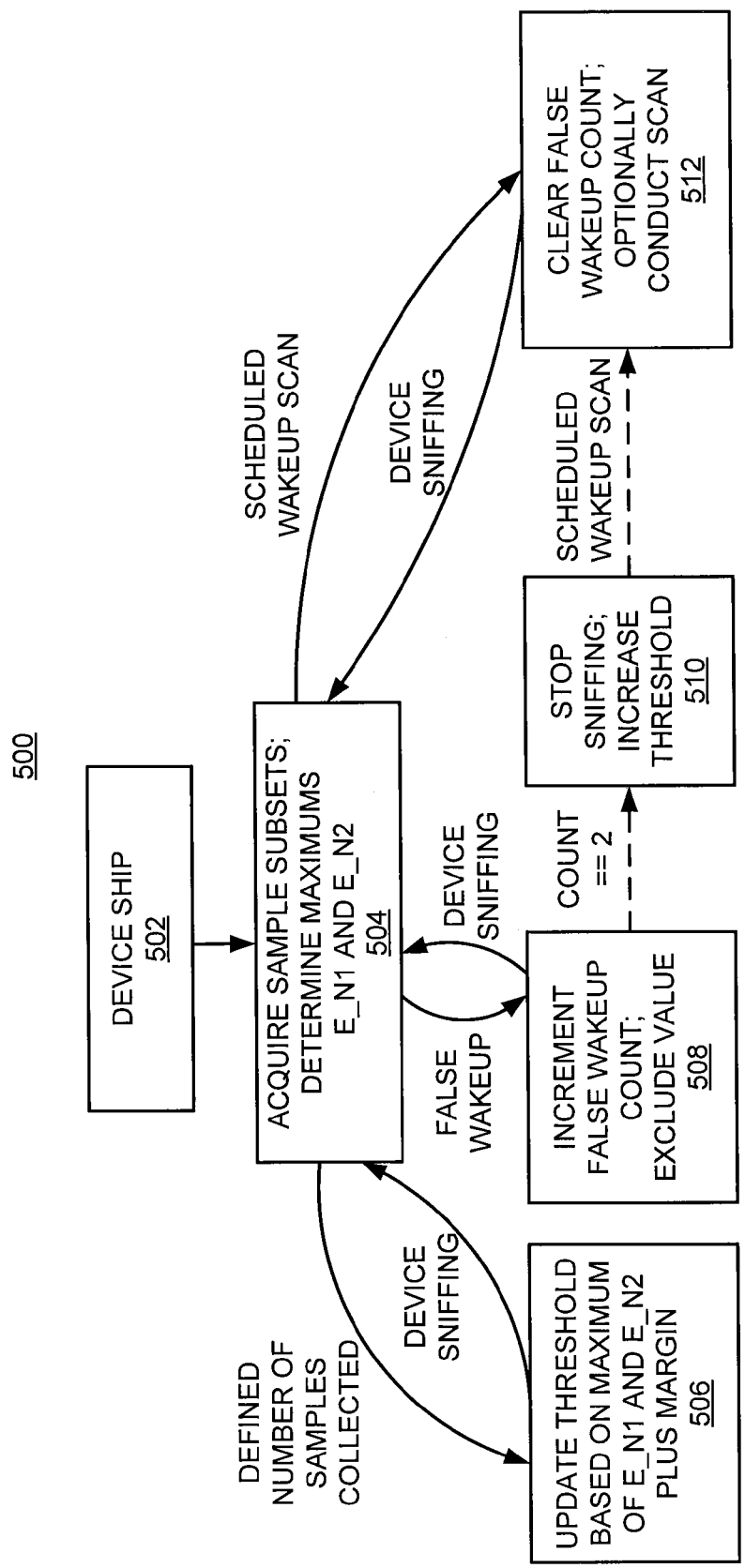
FIG. 5 is a flowchart of an embodiment of a threshold adaptation algorithm.

FIG. 5 illustrates an embodiment of an algorithm 500 that may be employed, for example, to adapt a threshold in response to changes in environmental conditions and/or device conditions. For example, in some aspects the automatically adjusted threshold provided by the algorithm 500 may have a long wakeup range (e.g., a lower threshold) in low noise environments and a short wakeup range (e.g., a higher threshold) in noisier environments.

Briefly, the algorithm 500 may adapt the threshold every time a defined number (e.g., 500) of new background samples (e.g., noise level values) are collected in conjunction with a previous collection of the defined number of background samples. This adaptation operation may increase or decrease the threshold depending on a maximum energy level (e.g., noise level) represented by the samples. In addition, if 2 false wakeups occur within a defined period of time (e.g., two hours), the threshold may be automatically increased. In addition, once the second false wakeup is detected, sample sniffing may be disabled for the remainder of that defined period of time.

As represented by block 502, when the implantable device 102 is shipped from the manufacturer, several parameters of the implantable device 102 may be set to default settings. For example, the threshold (e.g., a sniff threshold) may be set to a default value that is defined relative to determined or estimated background noise levels and target signal levels. In some embodiments this default value may be set to a value that is slightly less than a maximum energy level detectable by the implantable device 102. As a specific example, in an implantable device 102 that utilizes a 6-bit analog digital converter ("ADC"), the default value may be set to 0x30. Similarly, maximum sample values E_N1 and E_N2 associated with different sample subsets may be set to the same default value or some other default value. Finally, the econnect parameter 312 (FIG. 3) may be set to a default value such as 0.

As represented by block 504, after implant, the implanted device 102 is configured to acquire one or more sets of energy sample information (e.g., sample set(s) 326). This operation may comprise, for example, the background RF energy sniffing operations described above at FIG. 4. To enable the implanted device 102 to quickly commence threshold update operations after implant, the implanted device 102 may be configured to acquire the initial set of sample values at a rate that is faster than the normal background sample acquisition rate (e.g., that involve one sniff every 30 seconds).

In some aspects, each acquired set may comprise a defined number (e.g., 500) of energy sample values. The following describes a scenario where the implanted device 102 acquires two subsets of sample values. It should be appreciated, however, that other implementations may utilize a different number of sample subsets.

Figure 6:
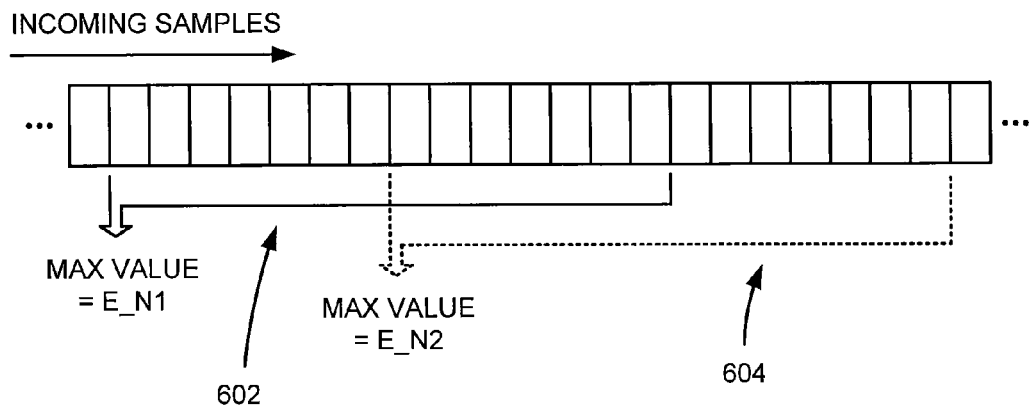
FIG. 6 is a simplified diagram illustrating an embodiment of data set acquisition.

The sample subsets may be acquired in various ways. For example, in some embodiments the implanted device 102 may acquire a sample subset, use the subset information, then acquire new subset information (e.g., discarding the prior reformation), use the new subset information, and so on. In some embodiments the implanted device 102 may acquire a sample subset through the use of a sliding sampling window. FIG. 6 illustrates an example of overlapping sliding sampling windows. Here, first and second sliding windows 602 and 604 are used to illustrate the relative timing of two overlapping sample subsets. It should be appreciated that FIG. 6 illustrates but one example of sample subsets and that sample subsets may be defined in other ways in accordance with the teachings herein.

As mentioned above at FIG. 4, the sample processor 328 may determine a maximum value associated with each sample subset 326. For example, the sample processor 328 may determine a maximum sample value E_N1 associated with a first sample subset (e.g., sliding window 602) and determine a maximum sample value E_N2 associated with a second sample subset (e.g., sliding window 604).

A maximum sample value associated with a given sliding window may be generated in various ways. For example, in some implementations the sample processor 328 may simply maintain a single value that represents the maximum value seen over a given window of data. Thus, as each new sample value is added to the set, the sample processor 328 may compare that value with the current maximum value and update the current maximum value, as necessary. In addition, when a sample that defined the current maximum value is shifted out of the current sample set, the sample processor 328 may reset the current maximum value based on the highest sample value that remains in the set.

As represented by block 506 of FIG. 5, once the defined number of samples is collected and the maximum sample values E_N1 and E_N2 are determined, the implanted device 102 may update the threshold 308 based on the maximum sample values E_N1 and E_N2. For example, the sample processor 328 may identify the maximum of E_N1 and E_N2 to define a maximum energy level and the threshold adapter 322 may set the threshold 308 to this maximum energy level plus a safety margin (e.g., 2 ADC counts).

In some embodiments the initial value for the threshold 308 may be determined based on one of the maximum sample values (e.g., E_N1). For example, upon implant or some other event that resets the contents of the subsets, after the data samples for a first one of the subsets are acquired and the maximum value determined for that subset, the operations of block 506 may simply involve setting the threshold 308 to that maximum value plus the safety margin. Then, after the data samples for the second one of the subsets are acquired and the maximum value determined for that subset, the operations of block 506 may involve selecting the maximum of the two maximum values associated with the two subsets as described above.

After the threshold 308 is updated, the implanted device 102 continues to perform its background device sniffing operations at block 504. That is, implanted device 102 may continue to acquire samples, update the subsets, and update the maximum sample values.

The implanted device 102 may therefore regularly adapt the threshold 308 at block 506 based on the signals that are currently being sensed. Consequently, in the event there is a change in environmental conditions (e.g., as discussed herein) at the implanted device 102, the threshold 308 may be increased or decreased as the sensed energy associated with these conditions increases or decreases. Thus, when the implanted device 102 is in a relatively noisy RF environment, the threshold 308 may be set to a higher value thereby decreasing the RF detection sensitivity of the implanted device 102. Conversely, when the implanted device 102 is in a relatively quiet RF environment, the threshold 308 may be set to a lower value thereby increasing the RF detection sensitivity. By adapting the threshold in this manner, the implanted device 102 may be able to effectively identify target signals in various environments.

As represented by block 508, in the event a false wakeup is detected, the false wakeup count 320 may be incremented. In conjunction with this operation, the sample value that triggered the false wakeup may be excluded from the corresponding sample set as background noise. The implanted device 102 may then continue to perform its background device sniffing operations at block 504.

In the event that a defined number of false wakeups (e.g., two or more) are detected within a defined period of time (e.g., two hours), the operational flow may proceed from block 508 to block 510. In some aspects, an increase in the number of false wakeups detected over a given period of time may result from an increase in the noise in the current environment, a change in the electrical characteristics of the implant pocket, the patient moving to a noisier environment, or some other factor. Consequently, the implanted device 102 may temporarily suspend the RF sniffing operations of the receiver 302 to avoid sample collection under these noisier conditions as indicated at block 510.

In addition, the implanted device 102 may further adapt its detection sensitivity based on the current operating environment (e.g., noise or interference that causes too many false wakeups). For example, the implanted device 102 may automatically increase the current threshold 308 by a defined adjustment value (e.g., 1 ADC count). By reducing the detection sensitivity of the implanted device 102 in this way, the probability of subsequent false wakeups may be reduced.

Various criteria may be employed to return the implanted device 102 to its normal operating state. For example, in some embodiments the implanted device 102 may remain in the state associated with block 510 for a defined period of time. FIG. 5 illustrates embodiment where the implanted device 102 transitions to the operations of block 512 at a specified point in time. For example, the implanted device 102 may employ scheduled wakeup scan times that are used to ensure that the implanted device 102 performs a comprehensive scan for signals from the external device 104 at some minimal time interval (e.g., at least once every two hours). Accordingly, in this example, the operational flow of FIG. 5 will transition from block 510 and 512 at the next scheduled wakeup scan time.

At block 512, the implanted device 102 clears the false wakeup counter. In addition, in some embodiments the implanted device 102 may set the threshold 308 back to its prior value at block 512 (e.g., by decrementing the threshold 308 by 1 ADC count). The implanted device 102 may then continue to perform its background device sniffing operations at block 504.

In some embodiments, the scheduled wakeup scan time interval (or some other suitable time interval) may be used to clear the false wakeup count on a regular basis. For example, in the event the false wakeup count did not reach a value of 2 before invocation of a scheduled wakeup scan (e.g., as represented by the transition from block 504 to 512) the false wakeup count may be reset to zero at block 512.

It should be appreciated that the operations described above may be modified in various ways. For example, in some embodiments the implanted device 102 may perform a scheduled wakeup scan when there is a transition from block 510 to block 512. In some embodiments, the implanted device 102 may elect to perform this scan if the current value of the threshold 308 is greater than or equal to the value of econnect 312 at block 512. Here, the implanted device 102 may determine the current value for econnect 312 in the event communication is established with the external device 104. In some embodiments, the implanted device 102 may elect to lower the threshold 308 or take some other action in such a case.

Figure 7:
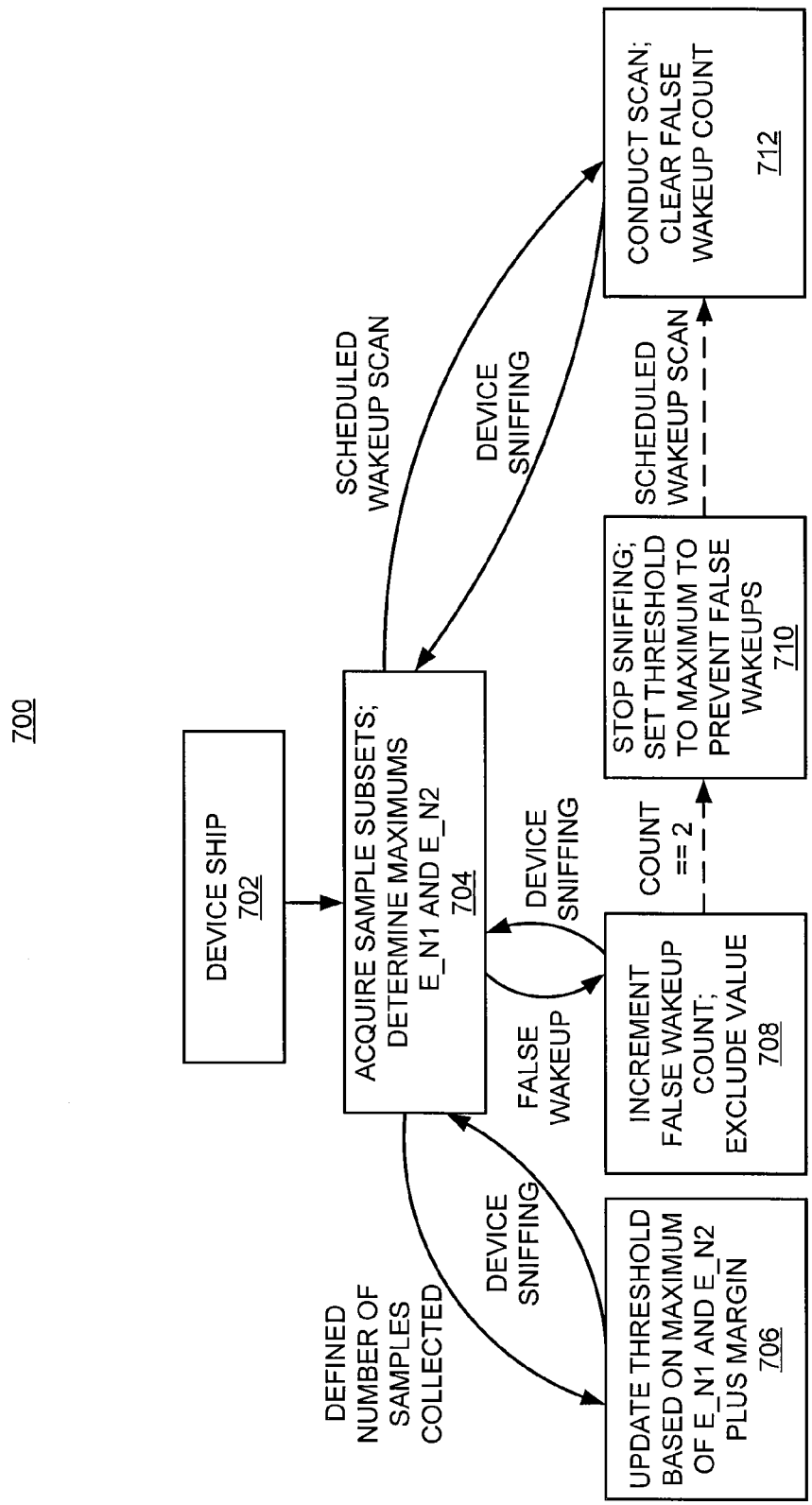
FIG. 7 is a flowchart of an embodiment of a threshold adaptation algorithm.

FIG. 7 illustrates another embodiment where an algorithm 700 is used to adapt a threshold. In some aspects, the algorithm 700 is more conservative (e.g., less sensitive) than the algorithm 500. Hence, in some cases the algorithm 700 may be employed in noisier environments. Here, the operations associated with blocks 702, 704, 706, and 708 may be the same as or similar to the operations of blocks 502, 504, 506, and 508 of algorithm 500. In this case, however, different operations are invoked in the event a defined number of false wakeups are detected within a defined period of time.

For example, at block 710, the receive mode controller 310 (FIG. 3) may disable RF sniffing operations and the threshold adapter 322 may set the threshold 308 to a maximum value. In this case, sniffing may be disabled based on an assumption that the high level of noise in the current environment would result in corruption of the sample subsets if samples were to be taken at this time. The wakeups may be disabled to prevent this noise from causing additional false wakeups and unnecessarily draining the battery of the implanted device 102.

In addition, at block 712 the implanted device 102 may always perform a scheduled wakeup scan in this case. That is, the sniffing and wakeups will be disabled for the entire period of time up to the next scheduled wakeup scan time represented by block 712.

Device sniffing operations may then be re-enabled when the operational flow returns back to block 704. In some embodiments, the implanted device 102 reacquires the sample subsets at block 704 in the event the sniffing and wakeup operations were disabled at block 710. For example, the information associated with each buffer may be cleared and new sample information (e.g., 500 samples) acquired for each subset. In this way, any sample information associated with a transient noise and/or interference condition may be discarded and new information quickly acquired after the transient condition passes. Here, the threshold 308 may remain at the maximum value until a new value for the threshold 308 is calculated at block 706. In some embodiments this new sample information may be acquired more rapidly than the normal background data acquisition rate (e.g., as discussed above). Also, in some embodiments the threshold 308 may initially be defined based on $E\_N1$ after its sample subset is acquired (e.g., as discussed above in conjunction with FIG. 5). In this case, after the sample subset associated with $E\_N2$ is acquired, in subsequent operations the threshold 308 is defined based on $E\_N1$ and $E\_N2$ as described above.

The above operations may be modified in various ways. For example, in some embodiments the operational flow may transition from block 710 to block 712 based on some other timing interval (e.g., an estimated duration of a transient noise condition) or based on some other trigger (e.g., a determination that a transient noise condition has ceased). In addition, operations relating to econnect 308 may be performed at block 712 as discussed above.

Figure 8:
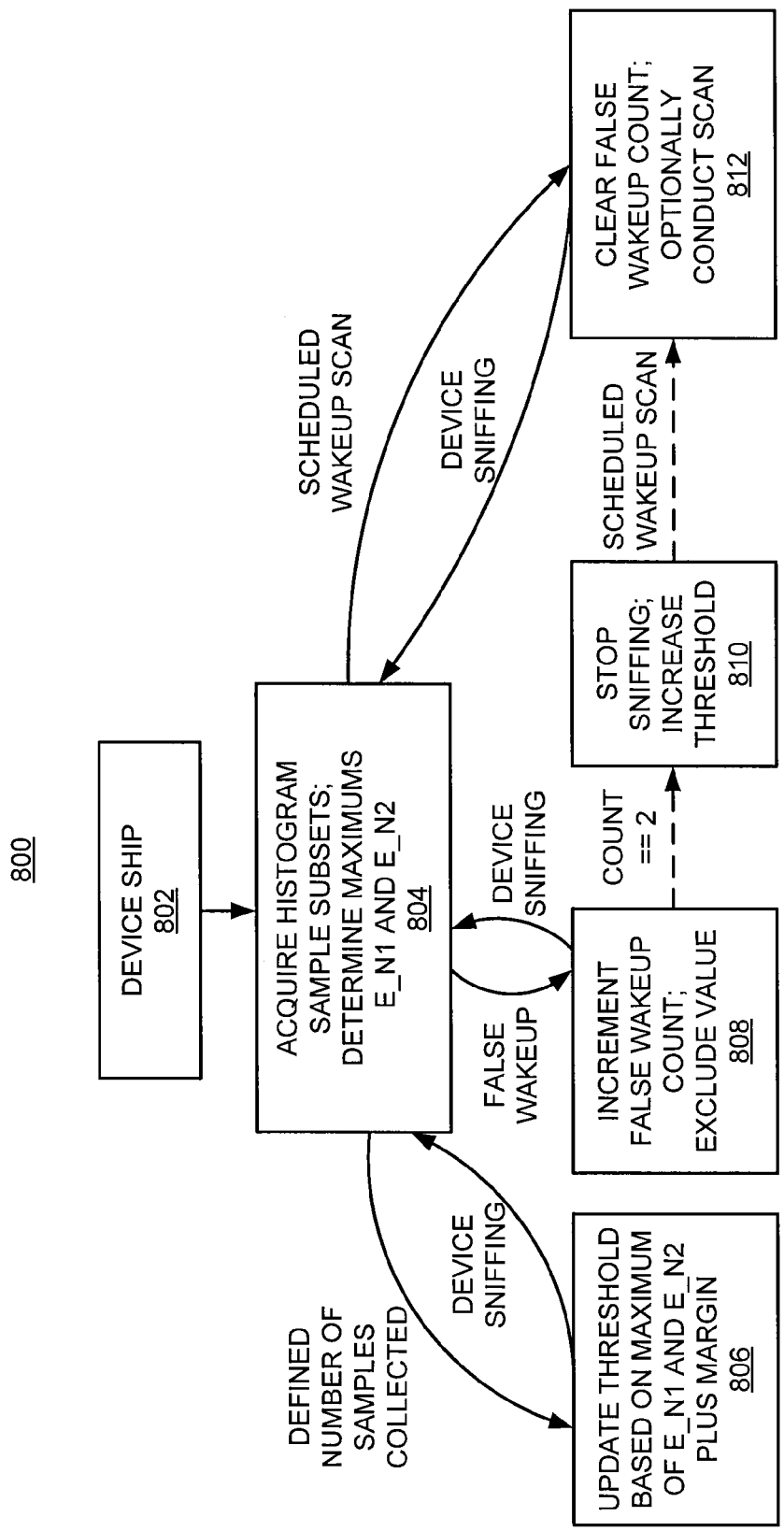
FIG. 8 is a flowchart of an embodiment of a threshold adaptation algorithm.

FIG. 8 illustrates an embodiment of an algorithm 800 that adapts a threshold based on histogram information. In this case, histogram-related operations are used to define the maximum sample values $E\_N1$ and $E\_N2$ at block 804. For example, a first histogram that is used to define $E\_N1$ may be based on a first sample set (e.g., 500 samples) and a second histogram that is used to define $E\_N2$ may be based on a second sample set (e.g., 500 samples). The remaining operations associated with blocks 802, 806, 808, 810, and 812 may be the same as or similar to the operations of blocks 502, 506, 508, 510, and 512 of algorithm 500.

Figure 9:
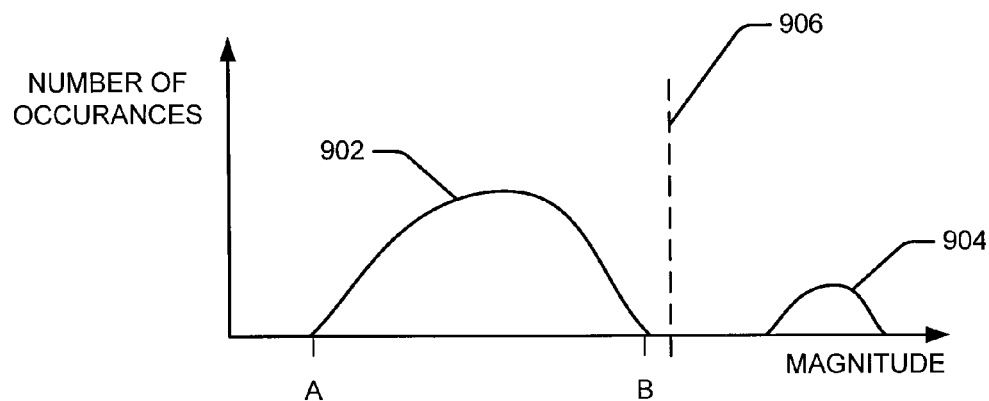
FIG. 9 is a simplified diagram illustrating an embodiment of a histogram.

FIG. 9 illustrates, in a simplified manner, sample plots 902 and 904 of histogram information. Here, the x-axis represents sample magnitude and the y-axis represents the number of occurrences of a given sample magnitude. The plot 902 may represent sampled energy associated with intrinsic noise (e.g., intrinsic noise of the receiver such as thermal noise or crosstalk). The plot 904 may represent environmental noise (e.g., interfering signals from one or more devices in the vicinity of the implanted device 102).

It should be appreciated that energy information may be distributed in various ways in the histogram depending on the current conditions. For example, in some cases the plot 902 may represent sampled energy associated with the intrinsic noise and environmental noise while the plot 904 may represent sampled energy associated with a target signal.

In some aspects, a maximum energy level may be defined based on a tail (e.g., a first tail) of the histogram information. In other words, at block 804 the algorithm 800 (e.g., by operation of the sample processor 328) identifies the maximum value of the low-end non-zero value set (sample set). In the example FIG. 9, the plot 902 represented this value set. The sample processor 328 may identify this value as follows. Starting with the lowest value in the sample set, the sample processor 328 will search for the first value with a non-zero occurrence (e.g., point A in FIG. 9). The sample processor 328 will then determine the value that is a non-zero occurrence before a zero occurrence value. This is point B in FIG. 9. Thus, assuming FIG. 9 corresponds to the first sample set, $E\_N1$ may be set to the magnitude corresponding to point B. Similar operations are then performed for the second histogram (based on the second data set). Thus, the operations of block 804 may provide $E\_N1$ that comprises the maximum value in the low-end sample set for the first histogram and $E\_N2$ that comprises the maximum value in the low-end sample set for the second histogram At block 806, after the sample processor 329 identifies the greater of $E\_N1$ or $E\_N2$, the threshold adapter 322 sets the threshold 308 to this maximum energy level plus a defined safety margin (e.g., 2 ADC counts) as described above in conjunction with FIG. 5. An example of such a threshold value is represented by the line 906 in FIG. 9.

In some aspects, the algorithm 800 may provide higher sensitivity than the algorithm 500 and the algorithm 700. For example, in some aspects the algorithm 800 may set the threshold 308 to a value that is just above the intrinsic noise. Thus, the algorithm 800 may be capable of distinguishing the intrinsic noise from environmental noise and/or target signals.

Based on the above it should be appreciated that the teachings herein may be advantageously employed to reduce the power consumed by an implanted device in conjunction with signal scanning operations. For example, through the use of the threshold adaptation techniques taught herein, the probability of missed target signals or false wakeups may be reduced. In some aspects, a system employing the teachings herein may have the benefit of setting an upper battery longevity hit limit due to false triggers on radio scans in adverse RF environments while maintaining good link sensitivity in a low noise radio environment. In addition, such a system may automatically adapt for changes in sensed energy levels due to implant pocket maturation and device hardware variation.

It also should be appreciated that the described operations may be modified and/or enhanced in various ways. For example, at least a portion of the threshold adaptation operations may occur within a clear channel assessment operation phase. In some aspects, such an operation may involve determining whether a communication channel to be used for communication between the devices 102 and 104 is currently available (e.g., is not being used by some other device). In some implementations, the channel condition information obtained during this phase may be used to determine the threshold. For example, the implanted device 102 may wait until the channel is clear before commencing a sniff operation.

In some implementations, the external device 104 may perform one or more operations relating to defining a threshold. For example, the external device 104 may be configured with appropriate functionality to sense energy (e.g., during a clear channel assessment operation) and generate a threshold and/or other threshold-related information based on the sensed energy as discussed herein. The external device 104 may then transmit this information (e.g., the threshold) to the implanted device 102 at some point in time.

In some implementations a threshold may be defined based on sensed RF energy and information (e.g., timing and/or energy level information) relating to one or more transmissions by an external device. For example, in a system including the devices 102 and 104, a threshold may be optimized for the devices by employing specific optimization steps such as correlating sample energy distribution (e.g., of an environmental spectrum) with knowledge about the transmission patterns of the external device 104. Here, with the external device 104 knowing the precise timing of when it transmitted energy, the threshold may be finely tuned by the system when borderline situations occur (e.g., when the relative margin between the environmental spectrum and the energy spectrum generated by the external device 104 is relatively small). For example, when this relative margin is within a certain range, the system may elect to define the threshold to be higher than the environmental spectrum (e.g., above a determined energy level associated with an environmental signal spectrum) but lower than the spectrum associated with transmission by the external device 104 (e.g., below a determined energy level associated with such a signal spectrum).

In some aspects, such a system-level optimization may involve information exchange between the devices 102 and 104. For example, the implanted device 102 may generate information (e.g., energy distribution information such as a histogram) based on sensed energy and transmit this information to the external device 104. The external device 104 may then define threshold information based on this transmitted information and the information the external device obtains relating to its transmission(s). For example, the external device 104 may correlate the information it receives with its transmission pattern to provide a finely-tuned threshold adjustment. The external device 104 may then transmit this threshold information to the implanted device 102. It should be appreciated that some of the above operations (e.g., sensing and/or providing threshold information such as a threshold adjustment or an actual threshold value) may be performed by the implanted device 102 and/or the external device 104.

A threshold as taught herein may be described in various ways. For example, such a threshold may comprise or be referred to as one or more of: a detection threshold, a noise threshold, an energy threshold, a wakeup threshold, a sniff threshold, or some other type of threshold.

The use of such a threshold also may be described in various ways. For example, such a use may be described as one or more of: determining whether to perform a more robust search, a more expensive search (e.g., in terms of power consumption and/or time), a higher-level search, a higher-level confirmation, or some other operation. Such a use also may be referred to as distinguishing a target signal from noise and/or interference, changing sensitivity, reducing the number of false wakeups, and so on.

As mentioned above, the teachings herein may be utilized in conjunction with an implantable cardiac device. The following describes an example of an implantable cardiac device (e.g., a stimulation device such as an implantable cardioverter defibrillator, a pacemaker, etc.) that is capable of being used in connection with the various embodiments that are described herein. It is to be appreciated and understood that other cardiac devices, including those that are not necessarily implantable, can be used and that the description below is given, in its specific context, to assist the reader in understanding, with more clarity, the embodiments described herein.

Figure 10:
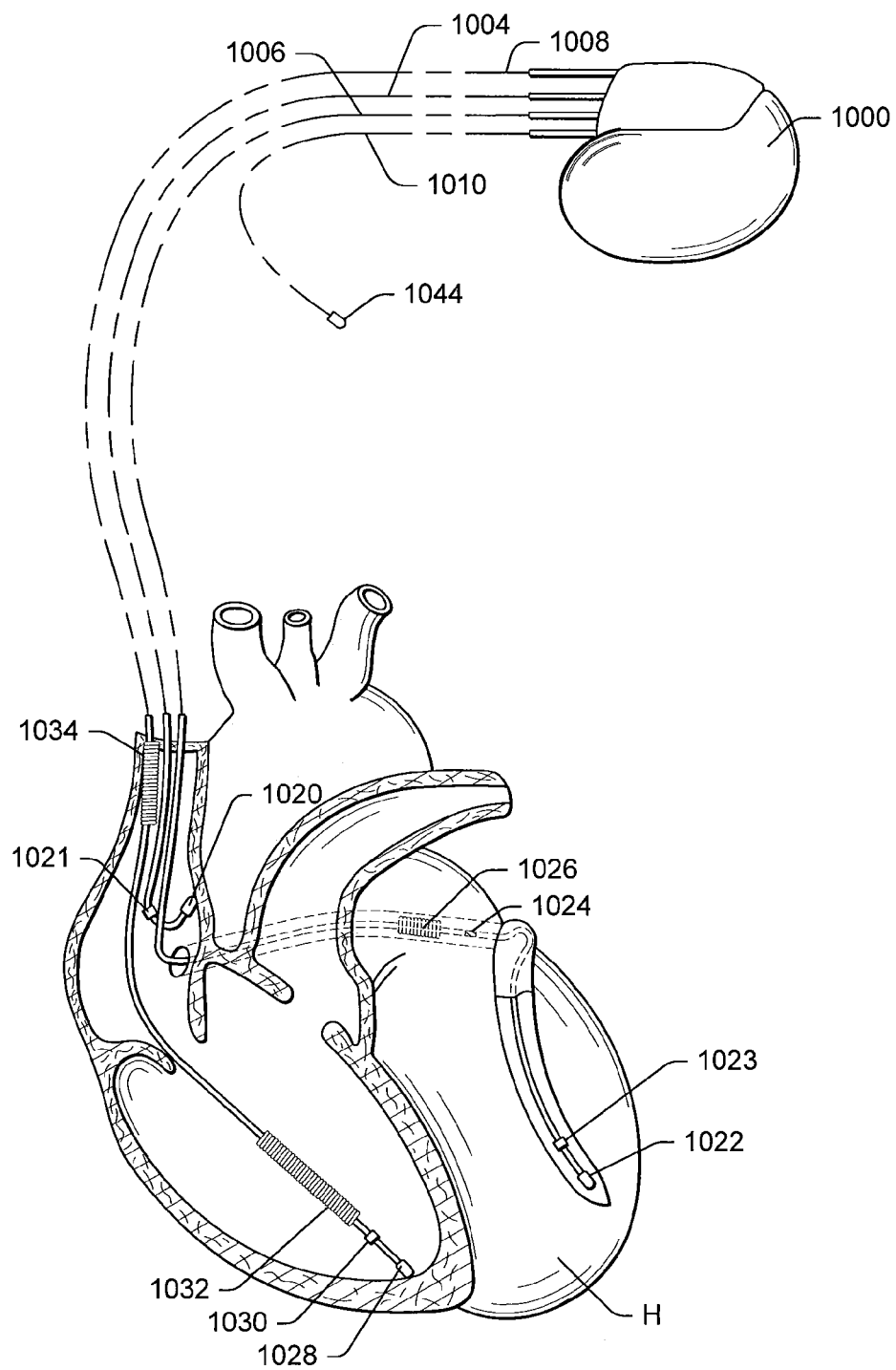
FIG. 10 is a simplified diagram of an embodiment of an implantable stimulation device in electrical communication with one or more leads implanted in a patient's heart for sensing conditions in the patient, delivering therapy to the patient, or providing some combination thereof.

FIG. 10 shows an exemplary implantable cardiac device 1000 in electrical communication with a patient's heart H by way of three leads 1004, 1006, and 1008, suitable for delivering multi-chamber stimulation and shock therapy. To sense atrial cardiac signals and to provide right atrial chamber stimulation therapy, the device 1000 is coupled to an implantable right atrial lead 1004 having, for example, an atrial tip electrode 1020, which typically is implanted in the patient's right atrial appendage or septum. FIG. 10 also shows the right atrial lead 1004 as having an optional atrial ring electrode 1021.

To sense left atrial and ventricular cardiac signals and to provide left chamber pacing therapy, the device 1000 is coupled to a coronary sinus lead 1006 designed for placement in the coronary sinus region via the coronary sinus for positioning one or more electrodes adjacent to the left ventricle, one or more electrodes adjacent to the left atrium, or both. As used herein, the phrase "coronary sinus region" refers to the vasculature of the left ventricle, including any portion of the coronary sinus, the great cardiac vein, the left marginal vein, the left posterior ventricular vein, the middle cardiac vein, the small cardiac vein or any other cardiac vein accessible by the coronary sinus.

Accordingly, an exemplary coronary sinus lead 1006 is designed to receive atrial and ventricular cardiac signals and to deliver left ventricular pacing therapy using, for example, a left ventricular tip electrode 1022 and, optionally, a left ventricular ring electrode 1023; provide left atrial pacing therapy using, for example, a left atrial ring electrode 1024; and provide shocking therapy using, for example, a left atrial coil electrode 1026 (or other electrode capable of delivering a shock). For a more detailed description of a coronary sinus lead, the reader is directed to U.S. Pat. No. 5,466,254, "Coronary Sinus Lead with Atrial Sensing Capability" (Helland), which is incorporated herein by reference.

The device 1000 is also shown in electrical communication with the patient's heart H by way of an implantable right ventricular lead 1008 having, in this implementation, a right ventricular tip electrode 1028, a right ventricular ring electrode 1030, a right ventricular (RV) coil electrode 1032 (or other electrode capable of delivering a shock), and a superior vena cava (SVC) coil electrode 1034 (or other electrode capable of delivering a shock). Typically, the right ventricular lead 1008 is transvenously inserted into the heart H to place the right ventricular tip electrode 1028 in the right ventricular apex so that the RV coil electrode 1032 will be positioned in the right ventricle and the SVC coil electrode 1034 will be positioned in the superior vena cava. Accordingly, the right ventricular lead 1008 is capable of sensing or receiving cardiac signals, and delivering stimulation in the form of pacing and shock therapy to the right ventricle.

The device 1000 is also shown in electrical communication with a lead 1010 including one or more components 1044 such as a physiologic sensor. The component 1044 may be positioned in, near or remote from the heart.

It should be appreciated that the device 1000 may connect to leads other than those specifically shown. In addition, the leads connected to the device 1000 may include components other than those specifically shown. For example, a lead may include other types of electrodes, sensors or devices that serve to otherwise interact with a patient or the surroundings.

Figure 11:
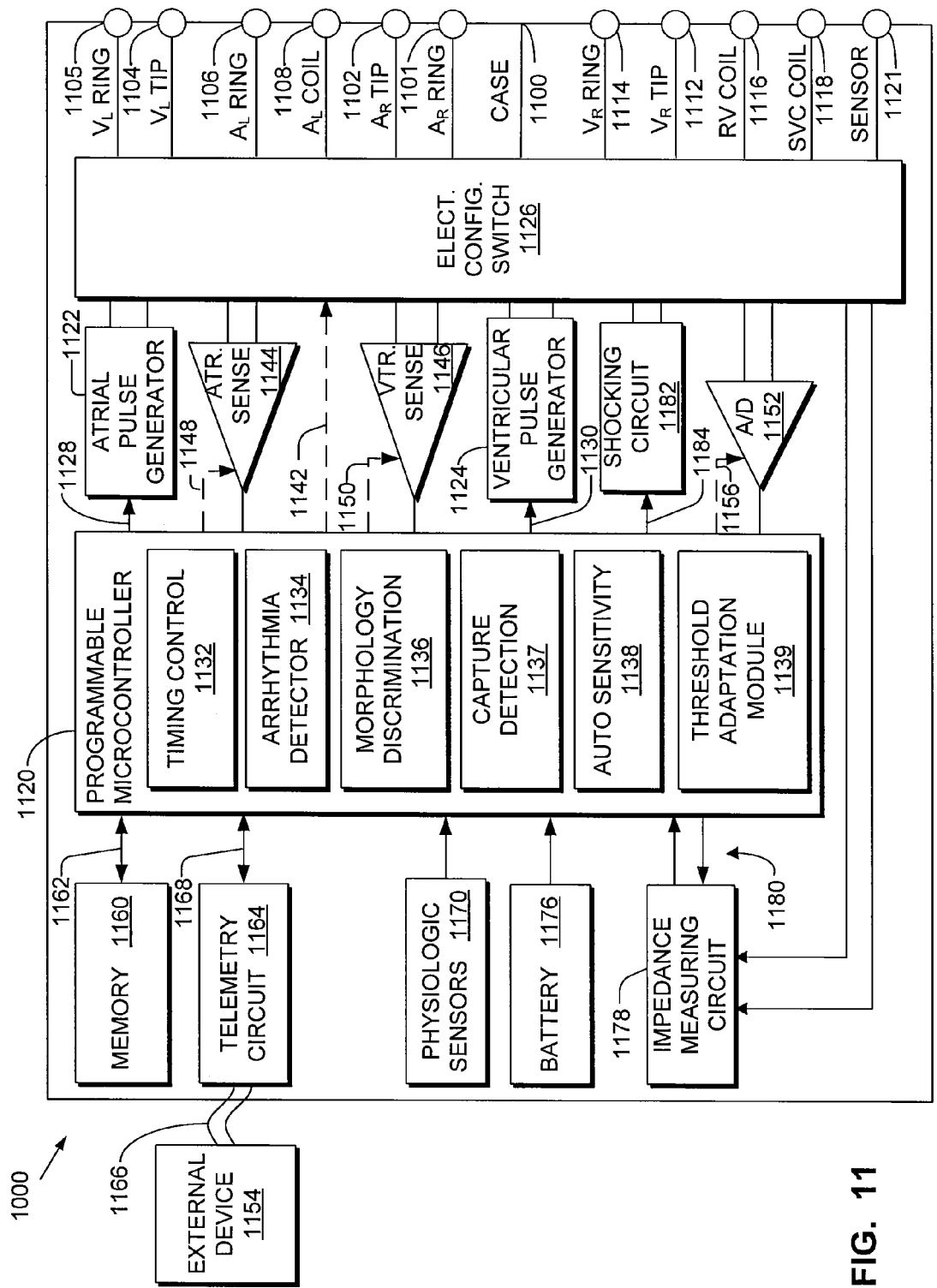
FIG. 11 is a simplified functional block diagram of an embodiment of an implantable cardiac device, illustrating basic elements that may be configured to sense conditions in the patient, deliver therapy to the patient, or provide some combination thereof.

FIG. 11 depicts an exemplary, simplified block diagram illustrating sample components of the device 1000. The device 1000 may be adapted to treat both fast and slow arrhythmias with stimulation therapy, including cardioversion, defibrillation, and pacing stimulation. While a particular multi-chamber device is shown, it is to be appreciated and understood that this is done for illustration purposes. Thus, the techniques and methods described below can be implemented in connection with any suitably configured or configurable device. Accordingly, one of skill in the art could readily duplicate, eliminate, or disable the appropriate circuitry in any desired combination to provide a device capable of treating the appropriate chamber(s) with, for example, cardioversion, defibrillation, and pacing stimulation.

Housing 1100 for the device 1000 is often referred to as the "can", "case" or "case electrode", and may be programmably selected to act as the return electrode for all "unipolar" modes. The housing 1100 may further be used as a return electrode alone or in combination with one or more of the coil electrodes 1026, 1032 and 1034 for shocking purposes. Housing 1100 further includes a connector (not shown) having a plurality of terminals 1101, 1102, 1104, 1105, 1106, 1108, 1112, 1114, 1116 and 1118 (shown schematically and, for convenience, the names of the electrodes to which they are connected are shown next to the terminals). The connector may be configured to include various other terminals (e.g., terminal 1121 coupled to a sensor or some other component) depending on the requirements of a given application.

To achieve right atrial sensing and pacing, the connector includes, for example, a right atrial tip terminal (AR TIP) 1102 adapted for connection to the right atrial tip electrode 1020. A right atrial ring terminal (AR RING) 1101 may also be included and adapted for connection to the right atrial ring electrode 1021. To achieve left chamber sensing, pacing, and shocking, the connector includes, for example, a left ventricular tip terminal (VL TIP) 1104, a left ventricular ring terminal (VL RING) 1105, a left atrial ring terminal (AL RING) 1106, and a left atrial shocking terminal (AL COIL) 1108, which are adapted for connection to the left ventricular tip electrode 1022, the left ventricular ring electrode 1023, the left atrial ring electrode 1024, and the left atrial coil electrode 1026, respectively.

To support right chamber sensing, pacing, and shocking, the connector further includes a right ventricular tip terminal (VR TIP) 1112, a right ventricular ring terminal (VR RING) 1114, a right ventricular shocking terminal (RV COIL) 1116, and a superior vena cava shocking terminal (SVC COIL) 1118, which are adapted for connection to the right ventricular tip electrode 1028, the right ventricular ring electrode 1030, the RV coil electrode 1032, and the SVC coil electrode 1034, respectively.

At the core of the device 1000 is a programmable microcontroller 1120 that controls the various modes of stimulation therapy. As is well known in the art, microcontroller 1120 typically includes a microprocessor, or equivalent control circuitry, designed specifically for controlling the delivery of stimulation therapy, and may further include memory such as RAM, ROM and flash memory, logic and timing circuitry, state machine circuitry, and I/O circuitry. Typically, microcontroller 1120 includes the ability to process or monitor input signals (data or information) as controlled by a program code stored in a designated block of memory. The type of microcontroller is not critical to the described implementations. Rather, any suitable microcontroller 1120 may be used that carries out the functions described herein. The use of microprocessor-based control circuits for performing timing and data analysis functions are well known in the art.

Representative types of control circuitry that may be used in connection with the described embodiments can include the microprocessor-based control system of U.S. Pat. No. 4,940,052 (Mann et al.), the state-machine of U.S. Pat. No. 4,712,555 (Thornander et al.) and U.S. Pat. No. 4,944,298 (Sholder), all of which are incorporated by reference herein. For a more detailed description of the various timing intervals that may be used within the device and their inter-relationship, see U.S. Pat. No. 4,788,980 (Mann et al.), also incorporated herein by reference.

FIG. 11 also shows an atrial pulse generator 1122 and a ventricular pulse generator 1124 that generate pacing stimulation pulses for delivery by the right atrial lead 1004, the coronary sinus lead 1006, the right ventricular lead 1008, or some combination of these leads via an electrode configuration switch 1126. It is understood that in order to provide stimulation therapy in each of the four chambers of the heart, the atrial and ventricular pulse generators 1122 and 1124 may include dedicated, independent pulse generators, multiplexed pulse generators, or shared pulse generators. The pulse generators 1122 and 1124 are controlled by the microcontroller 1120 via appropriate control signals 1128 and 1130, respectively, to trigger or inhibit the stimulation pulses.

Microcontroller 1120 further includes timing control circuitry 1132 to control the timing of the stimulation pulses (e.g., pacing rate, atrio-ventricular (A-V) delay, atrial interconduction (A-A) delay, or ventricular interconduction (V-V) delay, etc.) or other operations, as well as to keep track of the timing of refractory periods, blanking intervals, noise detection windows, evoked response windows, alert intervals, marker channel timing, etc., as known in the art.

Microcontroller 1120 further includes an arrhythmia detector 1134. The arrhythmia detector 1134 may be utilized by the device 1000 for determining desirable times to administer various therapies. The arrhythmia detector 1134 may be implemented, for example, in hardware as part of the microcontroller 1120, or as software/firmware instructions programmed into the device 1000 and executed on the microcontroller 1120 during certain modes of operation.

Microcontroller 1120 may include a morphology discrimination module 1136, a capture detection module 1137 and an auto sensitivity module 1138. These modules are optionally used to implement various exemplary recognition algorithms or methods. The aforementioned components may be implemented, for example, in hardware as part of the microcontroller 1120, or as software/firmware instructions programmed into the device 1000 and executed on the microcontroller 1120 during certain modes of operation.

The electrode configuration switch 1126 includes a plurality of switches for connecting the desired terminals (e.g., that are connected to electrodes, coils, sensors, etc.) to the appropriate I/O circuits, thereby providing complete terminal and, hence, electrode programmability. Accordingly, switch 1126, in response to a control signal 1142 from the microcontroller 1120, may be used to determine the polarity of the stimulation pulses (e.g., unipolar, bipolar, combipolar, etc.) by selectively closing the appropriate combination of switches (not shown) as is known in the art.

Atrial sensing circuits (ATR. SENSE) 1144 and ventricular sensing circuits (VTR. SENSE) 1146 may also be selectively coupled to the right atrial lead 1004, coronary sinus lead 1006, and the right ventricular lead 1008, through the switch 1126 for detecting the presence of cardiac activity in each of the four chambers of the heart. Accordingly, the atrial and ventricular sensing circuits 1144 and 1146 may include dedicated sense amplifiers, multiplexed amplifiers, or shared amplifiers. Switch 1126 determines the "sensing polarity" of the cardiac signal by selectively closing the appropriate switches, as is also known in the art. In this way, the clinician may program the sensing polarity independent of the stimulation polarity. The sensing circuits (e.g., circuits 1144 and 1146) are optionally capable of obtaining information indicative of tissue capture.

Each sensing circuit 1144 and 1146 preferably employs one or more low power, precision amplifiers with programmable gain, automatic gain control, bandpass filtering, a threshold detection circuit, or some combination of these components, to selectively sense the cardiac signal of interest. The automatic gain control enables the device 1000 to deal effectively with the difficult problem of sensing the low amplitude signal characteristics of atrial or ventricular fibrillation.

The outputs of the atrial and ventricular sensing circuits 1144 and 1146 are connected to the microcontroller 1120, which, in turn, is able to trigger or inhibit the atrial and ventricular pulse generators 1122 and 1124, respectively, in a demand fashion in response to the absence or presence of cardiac activity in the appropriate chambers of the heart. Furthermore, as described herein, the microcontroller 1120 is also capable of analyzing information output from the sensing circuits 1144 and 1146, a data acquisition system 1152, or both. This information may be used to determine or detect whether and to what degree tissue capture has occurred and to program a pulse, or pulses, in response to such determinations. The sensing circuits 1144 and 1146, in turn, receive control signals over signal lines 1148 and 1150, respectively, from the microcontroller 1120 for purposes of controlling the gain, threshold, polarization charge removal circuitry (not shown), and the timing of any blocking circuitry (not shown) coupled to the inputs of the sensing circuits 1144 and 1146 as is known in the art.

For arrhythmia detection, the device 1000 utilizes the atrial and ventricular sensing circuits 1144 and 1146 to sense cardiac signals to determine whether a rhythm is physiologic or pathologic. It should be appreciated that other components may be used to detect arrhythmia depending on the system objectives. In reference to arrhythmias, as used herein, "sensing" is reserved for the noting of an electrical signal or obtaining data (information), and "detection" is the processing (analysis) of these sensed signals and noting the presence of an arrhythmia.

Timing intervals between sensed events (e.g., P-waves, R-waves, and depolarization signals associated with fibrillation) may be classified by the arrhythmia detector 1134 of the microcontroller 1120 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy"). Similar rules may be applied to the atrial channel to determine if there is an atrial tachyarrhythmia or atrial fibrillation with appropriate classification and intervention.

Cardiac signals or other signals may be applied to inputs of an analog-to-digital (A/D) data acquisition system 1152. The data acquisition system 1152 is configured (e.g., via signal line 1156) to acquire intracardiac electrogram ("IEGM") signals or other signals, convert the raw analog data into a digital signal, and store the digital signals for later processing, for telemetric transmission to an external device 1154, or both. For example, the data acquisition system 1152 may be coupled to the right atrial lead 1004, the coronary sinus lead 1006, the right ventricular lead 1008 and other leads through the switch 1126 to sample cardiac signals across any pair of desired electrodes.

The data acquisition system 1152 also may be coupled to receive signals from other input devices. For example, the data acquisition system 1152 may sample signals from a physiologic sensor 1170 or other components shown in FIG. 11 (connections not shown).

The microcontroller 1120 is further coupled to a memory 1160 by a suitable data/address bus 1162, wherein the programmable operating parameters used by the microcontroller 1120 are stored and modified, as required, in order to customize the operation of the device 1000 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart H within each respective tier of therapy. One feature of the described embodiments is the ability to sense and store a relatively large amount of data (e.g., from the data acquisition system 1152), which data may then be used for subsequent analysis to guide the programming of the device 1000.

Advantageously, the operating parameters of the implantable device 1000 may be non-invasively programmed into the memory 1160 through a telemetry circuit 1164 in telemetric communication via communication link 1166 with the external device 1154, such as a programmer, transtelephonic transceiver, a diagnostic system analyzer or some other device. The microcontroller 1120 activates the telemetry circuit 1164 with a control signal (e.g., via bus 1168). The telemetry circuit 1164 advantageously allows intracardiac electrograms and status information relating to the operation of the device 1000 (as contained in the microcontroller 1120 or memory 1160) to be sent to the external device 1154 through an established communication link 1166.

The device 1000 can further include one or more physiologic sensors 1170. In some embodiments the device 1000 may include a "rate-responsive" sensor that may provide, for example, information to aid in adjustment of pacing stimulation rate according to the exercise state of the patient. One or more physiologic sensors 1170 (e.g., a pressure sensor) may further be used to detect changes in cardiac output, changes in the physiological condition of the heart, or diurnal changes in activity (e.g., detecting sleep and wake states). Accordingly, the microcontroller 1120 responds by adjusting the various pacing parameters (such as rate, A-V Delay, V-V Delay, etc.) at which the atrial and ventricular pulse generators 1122 and 1124 generate stimulation pulses.

While shown as being included within the device 1000, it is to be understood that a physiologic sensor 1170 may also be external to the device 1000, yet still be implanted within or carried by the patient. Examples of physiologic sensors that may be implemented in conjunction with the device 1000 include sensors that sense respiration rate, pH of blood, ventricular gradient, oxygen saturation, blood pressure and so forth. Another sensor that may be used is one that detects activity variance, wherein an activity sensor is monitored diurnally to detect the low variance in the measurement corresponding to the sleep state. For a more detailed description of an activity variance sensor, the reader is directed to U.S. Pat. No. 5,476,483 (Bornzin et al.), which patent is hereby incorporated by reference.

The one or more physiologic sensors 1170 may optionally include one or more of components to help detect movement (via, e.g., a position sensor or an accelerometer) and minute ventilation (via an MV sensor) in the patient. Signals generated by the position sensor and MV sensor may be passed to the microcontroller 1120 for analysis in determining whether to adjust the pacing rate, etc. The microcontroller 1120 may thus monitor the signals for indications of the patient's position and activity status, such as whether the patient is climbing up stairs or descending down stairs or whether the patient is sitting up after lying down.

The device 1000 additionally includes a battery 1176 that provides operating power to all of the circuits shown in FIG. 11. For a device 1000 which employs shocking therapy, the battery 1176 is capable of operating at low current drains (e.g., preferably less than 10 µA) for long periods of time, and is capable of providing high-current pulses (for capacitor charging) when the patient requires a shock pulse (e.g., preferably, in excess of 2 A, at voltages above 200 V, for periods of 10 seconds or more). The battery 1176 also desirably has a predictable discharge characteristic so that elective replacement time can be detected. Accordingly, the device 1000 preferably employs lithium or other suitable battery technology.

The device 1000 can further include magnet detection circuitry (not shown), coupled to the microcontroller 1120, to detect when a magnet is placed over the device 1000. A magnet may be used by a clinician to perform various test functions of the device 1000 and to signal the microcontroller 1120 that the external device 1154 is in place to receive data from or transmit data to the microcontroller 1120 through the telemetry circuit 1164.

The device 1000 further includes an impedance measuring circuit 1178 that is enabled by the microcontroller 1120 via a control signal 1180. The known uses for an impedance measuring circuit 1178 include, but are not limited to, lead impedance surveillance during the acute and chronic phases for proper performance, lead positioning or dislodgement; detecting operable electrodes and automatically switching to an operable pair if dislodgement occurs; measuring respiration or minute ventilation; measuring thoracic impedance for determining shock thresholds; detecting when the device 1000 has been implanted; measuring stroke volume; and detecting the opening of heart valves, etc. The impedance measuring circuit 1178 is advantageously coupled to the switch 1126 so that any desired electrode may be used.

In the case where the device 1000 is intended to operate as an implantable cardioverter/defibrillator (ICD) device, it detects the occurrence of an arrhythmia, and automatically applies an appropriate therapy to the heart aimed at terminating the detected arrhythmia. To this end, the microcontroller 1120 further controls a shocking circuit 1182 by way of a control signal 1184. The shocking circuit 1182 generates shocking pulses of low (e.g., up to 0.5 J), moderate (e.g., 0.5 J to 10 J), or high energy (e.g., 11 J to 40 J), as controlled by the microcontroller 1120. Such shocking pulses are applied to the patient's heart H through, for example, two shocking electrodes and as shown in this embodiment, selected from the left atrial coil electrode 1026, the RV coil electrode 1032 and the SVC coil electrode 1034. As noted above, the housing 1100 may act as an active electrode in combination with the RV coil electrode 1032, as part of a split electrical vector using the SVC coil electrode 1034 or the left atrial coil electrode 1026 (i.e., using the RV electrode as a common electrode), or in some other arrangement.

Cardioversion level shocks are generally considered to be of low to moderate energy level (so as to minimize pain felt by the patient), be synchronized with an R-wave, pertain to the treatment of tachycardia, or some combination of the above. Defibrillation shocks are generally of moderate to high energy level (i.e., corresponding to thresholds in the range of 5 J to 40 J), delivered asynchronously (since R-waves may be too disorganized), and pertaining to the treatment of fibrillation. Accordingly, the microcontroller 1120 is capable of controlling the synchronous or asynchronous delivery of the shocking pulses.

As mentioned above, the device 1000 may include several components that provide threshold adaptation-related functionality as taught herein. For example, the telemetry circuit 1164 (e.g., a transceiver) may include one or more of the components of FIG. 3. Such components may include some or a portion of the functionality of the receiver 302, the transmitter 316, the receive mode controller 310, and the communication processor 314. In addition, the received sample set 326, the threshold 308, the false wakeup count 320, and econnect 312 may be stored in the memory 1160.

The microcontroller 1120 (e.g., a processor providing signal processing functionality) also may implement or support at least a portion of the threshold adaptation-related functionality discussed herein. For example, the microcontroller 1120 may comprise a threshold adaptation module 1139 that may provide a portion or all of the functionality relating to the threshold adapter 322, the sample processor 328, the false wakeup detector 318, the receive mode controller 310, and the communication processor 314.

It should be appreciated that various modifications may be incorporated into the disclosed embodiments based on the teachings herein. For example, the structure and functionality taught herein may be incorporated into different types of devices other than those types specifically described. In addition, various algorithms or techniques may be employed to provide a threshold adaptation scheme.

It should be appreciated from the above that the various structures and functions described herein may be incorporated into a variety of apparatuses (e.g., a stimulation device, a monitoring device, etc.) and implemented in a variety of ways. Different embodiments of the stimulation device may include a variety of hardware and software processing components. In some embodiments, hardware components such as processors, controllers, state machines, logic, or some combination of these components, may be used to implement the described components or circuits.

In some embodiments, code including instructions (e.g., software, firmware, middleware, etc.) may be executed on one or more processing devices to implement one or more of the described functions or components. The code and associated components (e.g., data structures and other components used by the code or used to execute the code) may be stored in an appropriate data memory that is readable by a processing device (e.g., commonly referred to as a computer-readable medium).

As mentioned above, some of the operations described herein may be performed by a device that is located externally with respect to the body of the patient. For example, an implanted device may send raw data or processed data to an external device that then performs additional processing, or vice versa.

The components and functions described herein may be connected or coupled in many different ways. The manner in which this is done may depend, in part, on whether and how the components are separated from the other components. In some embodiments some of the connections or couplings represented by the lead lines in the drawings may be in an integrated circuit, on a circuit board or implemented as discrete wires or in other ways.

The signals discussed herein may take various forms. For example, in some embodiments a signal may comprise electrical signals transmitted over a wire, light pulses transmitted through an optical medium such as an optical fiber or air, or RF waves transmitted through a medium such as air, and so on. In addition, a plurality of signals may be collectively referred to as a signal herein. The signals discussed above also may take the form of data. For example, in some embodiments an application program may send a signal to another application program. Such a signal may be stored in a data memory.

Moreover, the recited order of the blocks in the processes disclosed herein is simply an example of a suitable approach. Thus, operations associated with such blocks may be rearranged while remaining within the scope of the present disclosure. Similarly, the accompanying method claims present operations in a sample order, and are not necessarily limited to the specific order presented.

Also, it should be understood that any reference to elements herein using a designation such as "first," "second," and so forth does not generally limit the quantity or order of those elements. Rather, these designations may be used herein as a convenient method of distinguishing between two or more different elements or instances of an element. Thus, a reference to first and second elements does not mean that only two elements may be employed there or that the first element must precede the second element in some manner. Also, unless stated otherwise a set of elements may comprise one or more elements.

While certain embodiments have been described above in detail and shown in the accompanying drawings, it is to be understood that such embodiments are merely illustrative of and not restrictive of the teachings herein. In particular, it should be recognized that the teachings herein apply to a wide variety of apparatuses and methods. It will thus be recognized that various modifications may be made to the illustrated embodiments or other embodiments, without departing from the broad scope thereof. In view of the above it will be understood that the teachings herein are intended to cover any changes, adaptations or modifications which are within the scope of the disclosure.

What is claimed is:

1. A wireless communication method, comprising:
   sensing radio frequency energy;
   obtaining information that indicates an energy level used by an external communication device for a transmission; and
   defining, based on the sensed energy and the information, a threshold for identifying target radio frequency signals at an implanted medical device.

2. The method of claim 1, wherein the obtained information further indicates at least one time at which the transmission occurred.

3. The method of claim 1, wherein the definition of the threshold comprises correlating an energy distribution associated with the sensed energy with transmission timing patterns of the external communication device that are indicated by the obtained information.

4. The method of claim 1, further comprising:
   determining an energy level of an environmental signal spectrum associated with the sensed energy; and
   determining, based on the obtained information, an energy level of a signal spectrum associated with the transmission,
   wherein the definition of the threshold comprises setting the threshold to a level that is higher than the energy level of the environmental signal spectrum and lower than the energy level of a signal spectrum associated with the transmission.

5. The method of claim 1, further comprising:
   determining a relative margin between an environmental signal spectrum associated with the sensed energy and a signal spectrum associated with the transmission; and
   determining, based on the relative margin, whether to use the obtained information to adapt the threshold.

6. The method of claim 1, further comprising:
   transmitting information based on the sensed energy to the external communication device;
   defining a threshold adjustment at the external communication device based on the transmitted information and the obtained information; and
   transmitting the threshold adjustment to the implanted device.

7. A communication method for an implantable medical device, comprising:
   intermittently sensing radio frequency energy;
   generating a sample set comprising a defined number of energy sample values, wherein the enemy sample values indicate a plurality of enemy levels of the intermittently sensed radio frequency energy;
   determining a maximum energy level for the sample set based on identification of at least one of the energy sample values having a higher value than at least one other one of the energy samples values; and
   adapting a threshold based on the maximum energy level, wherein the adaptation of the threshold adjusts detection sensitivity associated with identifying target radio frequency signals in a current environment.

8. The method of claim 7, wherein the adaptation of the threshold is further based on a determination of whether a defined number of false wakeups occurred within a defined period of time.

9. The method of claim 8, further comprising temporarily suspending the sensing if the defined number of false wakeups occurred within the defined period of time.

10. The method of claim 9, further comprising:
    following the suspending of the sensing, resuming the sensing at a point in time based on a wakeup scan time interval;
    acquiring a new set of energy sample values upon resumption of the sensing; and
    re-adapting the threshold based on the new set of energy sample values.

11. The method of claim 7, wherein:
    the sample set comprises a plurality of subsets; and
    the determination of the maximum energy level comprises:
       determining a maximum sample value for each subset;
       identifying a maximum of the maximum sample values for the subsets; and
       setting the maximum energy level to the identified maximum.

12. The method of claim 11, wherein the subsets are defined based on sliding sample windows that partially overlap.

13. The method of claim 7, wherein the sample set comprises a histogram.

14. The method of claim 13, wherein:
    the histogram comprises a first tail; and
    the maximum energy level is based on the first tail of the histogram.

15. The method of claim 13, wherein:
    the histogram includes a low-end non-zero contiguous set of values; and
    the maximum energy level is based on a maximum value of the low-end non-zero contiguous set of values.

16. The method of claim 7, wherein the adaptation of the threshold further comprises setting the threshold to a maximum value to prevent false wakeups for a period of time.

17. The method of claim 16, further comprising acquiring a new set of sample values to change the threshold from the maximum value to a new value.

18. The method of claim 7, further comprising disabling the adaptation of the threshold based on the maximum energy level if a defined number of false wakeups occurred during a defined period of time.

19. The method of claim 1, further comprising:
performing a sniff operation to detect radio frequency signal energy during a low power operational mode;
performing a radio frequency scan operation if the detected radio frequency signal energy is greater than or equal to the threshold, wherein the radio frequency scan operation is longer in duration and/or consumes more power than the sniff operation; and
determining, based on the radio frequency scan operation, whether to commence communicating with a device that generated the detected radio frequency signal energy.

20. The method of claim 7, wherein:
the sensing comprises sensing environmental and/or intrinsic noise;
the energy sample values relate to energy levels of discrete samples of the environmental and/or intrinsic noise; and
the determination of the maximum energy level comprises taking a statistical measure of the energy sample values, whereby the adaptation of the threshold is further based on the statistical measure.

21. The method of claim 7, further comprising:
determining that a communication channel to be used for communication between the implantable medical device and an external device is not being used by another device; and
performing the sensing on the communication channel as a result of the determination that the communication channel is not being used.

22. The method of claim 7, further comprising:
temporarily suspending the sensing if a defined number of false wakeups occurred within a defined period of time; and
following the suspending of the sensing, resuming the sensing at a point in time based on a wakeup scan time interval.

23. An implantable medical apparatus, comprising:
a receiver configured to intermittently sense radio frequency energy, and configured to generate a sample set comprising a defined number of energy sample values, wherein the energy sample values indicate a plurality of energy levels of the intermittently sensed radio frequency energy;
a sample processor configured to determine a maximum energy level for the sample set based on identification of at least one of the energy sample values having a higher value than at least one other one of the energy sample values; and
a threshold adapter configured to adapt a threshold based on the maximum energy level, wherein the adaptation of the threshold adjusts detection sensitivity associated with identifying target radio frequency signals in a current environment.

24. The apparatus of claim 23, further comprising a false wakeup detector configured to determine whether a defined number of false wakeups occurred within a defined period of time, wherein the threshold adapter is further configured to adapt the threshold if the defined number of false wakeups occurred within the defined period of time.

25. The apparatus of claim 24, wherein the receiver is further configured to temporarily suspend the sensing if the defined number of false wakeups occurred within the defined period of time.

26. The apparatus of claim 23, wherein:
the sample set comprises a plurality of subsets; and
the sample processor is further configured to define the maximum energy level by:
determining a maximum sample value for each subset;
identifying a maximum of the maximum sample values for the subsets; and
setting the maximum energy level to the identified maximum.

27. The apparatus of claim 26, wherein the subsets are defined based on sliding sample windows that partially overlap.

28. The apparatus of claim 23, wherein the sample set comprises a histogram.

29. The apparatus of claim 28, wherein:
the histogram comprises a first tail; and
the sample processor is further configured to define the maximum energy level based on the first tail of the histogram.

30. The apparatus of claim 23, wherein the threshold adapter is further configured to set the threshold to a maximum value to prevent false wakeups for a period of time.

31. The apparatus of claim 23, wherein the threshold adapter is further configured to disable the adaptation of the threshold based on the maximum energy level if a defined number of false wakeups occurred during a defined period of time.

32. The apparatus of claim 23, wherein:
the receiver is further configured to perform a sniff operation to detect radio frequency signal energy during a low power operational mode;
the receiver is further configured to perform a radio frequency scan operation if the detected radio frequency signal energy is greater than or equal to the threshold;
the radio frequency scan operation is longer in duration and/or consumes more power than the sniff operation; and
the apparatus further comprises a communication processor configured to determine, based on the radio frequency scan operation, whether to commence communicating with a device that generated the detected radio frequency signal energy.

33. A wireless communication system, comprising:
an implantable medical device configured to:
sense radio frequency energy; and
transmit information based on the sensed energy; and
a communication device configured to:
receive the information transmitted by the implantable medical device;
obtain information that indicates an energy level used by the communication device for a transmission;
define threshold information for identifying target radio frequency signals at the implantable medical device based on the received information and the obtained information; and
transmit the threshold information to the implantable medical device.

34. The system of claim 33, wherein the obtained information further indicates at least one time at which the transmission occurred.

35. The system of claim 33, wherein the definition of the threshold information comprises correlating an energy distribution associated with the sensed energy with transmission timing patterns of the communication device that are indicated by the obtained information.

36. The system of claim 33, wherein the communication device is further configured to:
- determine an energy level of an environmental signal spectrum associated with the sensed energy; and
- determine, based on the obtained information, an energy level of a signal spectrum associated with the transmission by the communication device,
- wherein the definition of the threshold information comprises setting a threshold to a level that is higher than the energy level of the environmental signal spectrum and lower than the energy level of a signal spectrum associated with the transmission by the communication device.

37. The system of claim 33, wherein the communication device is further configured to:
- determine a relative margin between an environmental signal spectrum associated with the sensed energy and a signal spectrum associated with the transmission by the communication device; and
- determine, based on the relative margin, whether to use the obtained information to define the threshold information.

* * * * *